(12) United States Patent
Latham et al.

(10) Patent No.: US 7,067,298 B2
(45) Date of Patent: Jun. 27, 2006

(54) COMPOSITIONS AND METHODS OF USING A SYNTHETIC DNASE I

(75) Inventors: Gary Latham, Austin, TX (US); Jon Kemppainen, Austin, TX (US)

(73) Assignee: Ambion, Inc., Austin, TX (US)

( * ) Notice: Subject to any disclaimer, the term of this patent is extended or adjusted under 35 U.S.C. 154(b) by 366 days.

(21) Appl. No.: 10/420,345

(22) Filed: Apr. 22, 2003

(65) Prior Publication Data

US 2004/0219529 A1      Nov. 4, 2004

Related U.S. Application Data

(63) Continuation-in-part of application No. 10/404,023, filed on Mar. 31, 2003, now abandoned.

(51) Int. Cl.
*C12N 9/22* (2006.01)
*C12N 15/55* (2006.01)

(52) U.S. Cl. ............. 435/199; 435/255.5; 435/320.1; 536/23.2

(58) Field of Classification Search ............ 435/320.1, 435/255.5, 199; 536/23.2
See application file for complete search history.

(56) References Cited

OTHER PUBLICATIONS

Liao, T-H., et al. (1973) J. Biol. Chem. 248 (4), 1489-1495.*

* cited by examiner

*Primary Examiner*—Charles L. Patterson, Jr.
(74) *Attorney, Agent, or Firm*—Chalkov Flores, LLP; Edwin S. Flores; Daniel J. Chalker

(57) ABSTRACT

Compositions and method for making and using a synthetic bovine DNase I are disclosed. More particularly, the sbDNase I of the present invention is a versatile enzyme that cleaves DNA nonspecifically to release 5'-phosphorylated nucleotides. The sbDNase I molecules of the present invention find particular use in a wide range of molecular biology applications, including: degradation of contaminating DNA after RNA isolation; RNA clean-up prior to, or in conjunction with, RT-PCR after in vitro transcription; identification of protein binding sequences on DNA (DNase I footprinting); prevention of clumping when handling cultured cells; tissue dissociation and creation of fragmented DNA for in vitro recombination reactions.

23 Claims, 8 Drawing Sheets

```
ATGAAGATCGCAGCTTTCAACATCCGCACCTTCGGTGAAACCAAAATGTCCAACGCTACTCTGGCAAGCTACATTGT
TCGTATCGTGCGTCGTTACGACATCGTTCTGATCCAGGAGGTTAGGGACAGCCACCTGGTAGCTGTTGGTAAGCTGC
TGGACTACCTGAACCAGGATGACCCAAACACCTACCACTATGTAGTTAGCGAGCCGCTGGGCCGCAACAGCTACAAA
GAGCGCTACCTGTTTCTGTTCCGTCCGAACAAGGTTTCCGTGCTGGACACCTACCAGTACGACGACGGCTGCGAGTC
CTGCGGTAACGACAGCTTCAGCCGTGAGCCGGCTGTGGTTAAGTTCTCTTCCCACTCCACCAAGGTAAAGGAATTTG
CTATTGTTGCTCTGCACTCTGCACCATCCGACGCAGTAGCTGAGATTAACTCTCTGTACGATGTTTACCTGGATGTT
CAGCAGAAGTGGCACCTGAACGATGTAATGCTGATGGGCGATTTCAACGCTGACTGCAGCTACGTAACCTCCTCTCA
GTGGTCTTCCATCCGCCTGCGTACCAGCTCCACCTTCCAGTGGCTGATTCCGGACAGCGCTGACACCACTGCTACTT
CCACCAACTGCGCGTATGACCGTATCGTGGTTGCAGGTTCTCTGCTGCAGAGCTCTGTGGTTCCGGGCTCTGCAGCT
CCGTTTGACTTCCAAGCTGCATACGGTCTGAGCAACGAGATGGCTCTGGCAATCAGCGACCATTACCCGGTTGAGGT
GACCCTGACTTAA
```

Fig. 1

ATGAAGATCGCAGCTTTCAACATCCGCACCTTCGGTGAAACCAAAATGTCCAACGCTACTCTGGCAAGCTACATTGT
TCGTATCGTGCGTCGTTACGACATCGTTCTGATCCAGGAGGTTAGGGACAGCCACCTGGTAGCTGTTGGTAAGCTGC
TGGACTACCTGAACCAGGATGACCCAAACACCTACCACTATGTAGTTAGCGAGCCGCTGGGCCGCAACAGCTACAAA
GAGCGCTACCTGTTTCTGTTCCGTCCGAACAAGGTTTCCGTGCTGGACACCTACCAGTACGACGACGGCTGCGAGTC
CTGCGGTAACGACAGCTTCAGCCGTGAGCCGGCTGTGGTTAAGTTCTCTTCCCACTCCACCAAGGTAAAGGAATTTG
CTATTGTTGCTCTGCACTCTGCACCATCCGACGCAGTAGCTGAGATTAACTCTCTGTACGATGTTTACCTGGATGTT
CAGCAGAAGTGGCACCTGAACGATGTAATGCTGATGGGCGATTTCAACGCTGACTGCAGCTACGTAACCTCCTCTCA
GTGGTCTTCCATCCGCCTGCGTACCAGCTCCACCTTCCAGTGGCTGATTCCGGACAGCGCTGACACCACTGCTACTT
CCACCAACTGCGCGTATGACCGTATCGTGGTTGCAGGTTCTCTGCTGCAGAGCTCTGTGGTTCCGGGCTCTGCAGCT
CCGTTTGACTTCCAAGCTGCATACGGTCTGAGCAACGAGATGGCTCTGGCAATCAGCGACCATTACCCGGTTGAGGT
GACCCTGACTTAA

Fig. 2

ATGAAATACCTGCTGCCGACCGCTGCTGCTGGTCTGCTGCTCCTCGCTGCCCAGCCGGCGATGGCCATGGATATCGG
AATTAATTCGGATCCAATGAAGATCGCAGCTTTCAACATCCGCACCTTCGGTGAAACCAAAATGTCCAACGCTACTC
TGGCAAGCTACATTGTTCGTATCGTGCGTCGTTACGACATCGTTCTGATCCAGGAGGTTAGGGACAGCCACCTGGTA
GCTGTTGGTAAGCTGCTGGACTACCTGAACCAGGATGACCCAAACACCTACCACTATGTAGTTAGCGAGCCGCTGGG
CCGCAACAGCTACAAAGAGCGCTACCTGTTTCTGTTCCGTCCGAACAAGGTTTCCGTGCTGGACACCTACCAGTACG
ACGACGGCTGCGAGTCCTGCGGTAACGACAGCTTCAGCCGTGAGCCGGCTGTGGTTAAGTTCTCTTCCCACTCCACC
AAGGTAAAGGAATTTGCTATTGTTGCTCTGCACTCTGCACCATCCGACGCAGTAGCTGAGATTAACTCTCTGTACGA
TGTTTACCTGGATGTTCAGCAGAAGTGGCACCTGAACGATGTAATGCTGATGGGCGATTTCAACGCTGACTGCAGCT
ACGTAACCTCCTCTCAGTGGTCTTCCATCCGCCTGCGTACCAGCTCCACCTTCCAGTGGCTGATTCCGGACAGCGCT
GACACCACTGCTACTTCCACCAACTGCGCGTATGACCGTATCGTGGTTGCAGGTTCTCTGCTGCAGAGCTCTGTGGT
TCCGGGCTCTGCAGCTCCGTTTGACTTCCAAGCTGCATACGGTCTGAGCAACGAGATGGCTCTGGCAATCAGCGACC
ATTACCCGGTTGAGGTGACCCTGACTTAA

Fig. 3A

ATGAGATTTCCTTCAATTTTTACTGCTGTTTTATTCGCAGCATCCTCCGCATTAGCTGCTCCAGTCAACACTACAACAGAAGATGA
AACGGCACAAATTCCGGCTGAAGCTGTCATCGGTTACTCAGATTTAGAAGGGGATTTCGATGTTGCTGTTTTGCCATTTTCCAACA
GCACAAATAACGGGTTATTGTTTATAAATACTACTATTGCCAGCATTGCTGCTAAAGAAGAAGGGGTATCT<u>CTCGAG</u>AAGAGActg
aagatcgcagctttcaacatccgcaccttcggtgaaaccaaaatgtccaacgctactctggcaagctacattgttcgtatcgtgcg
tcgttacgacatcgttctgatccaggaggttagggacagccacctggtagctgttggtaagctgctggactacctgaaccaggatg
acccaaacacctaccactatgtagttagcgagccgctgggccgcaacagctacaaagagcgctacctgtttctgttccgtccgaac
aaggtttccgtgctggacacctaccagtacgacgacggctgcgagtcctgcggtaacgacagcttcagccgtgagccggctgtggt
taagttctcttcccactccaccaaggtaaaggaatttgctattgttgctctgcactctgcaccatccgacgcagtagctgagatta
actctctgtacgatgtttacctggatgttcagcagaagtggcacctgaacgatgtaatgctgatgggcgatttcaacgctgactgc
agctacgtaacctcctctcagtggtcttccatccgcctgcgtaccagctccaccttccagtggctgattccggacagcgctgacac
cactgctacttccaccaactgcgcgtatgaccgtatcgtggttgcaggttctctgctgcagagctctgtggttccgggctctgcag
ctccgtttgacttccaagctgcatacggtctgagcaacgagatggctctggcaatcagcgaccattacccggttgaggtgaccctg
actTAAG<u>CGGCCGC</u>

Fig. 3B

MRFPSIFTAVLFAASSALAAPVNTTTEDETAQIPAEAVIGYSDLEGDFDVAVLPFSNSTNNGLLFINTTIASIAAKEEGV

SLEKRLKIAAFNIRTFGETKMSNATLASYIVRIVRRYDIVLIQEVRDSHLVAVGKLLDYLNQDDPNTYHYVVSEPLGRNS
↓

YKERYLFLFRPNKVSVLDTYQYDDGCESCGNDSFSREPAVVKFSSHSTKVKEFAIVALHSAPSDAVAEINSLYDVYLDVQ

QKWHLNDVMLMGDFNADCSYVTSSQWSSIRLRTSSTFQWLIPDSADTTATSTNCAYDRIVVAGSLLQSSVVPGSAAPFDF

QAAYGLSNEMALAISDHYPVEVTLT

Fig. 4

```
Bovine     CTGAAGATAGCAGCCTTCAACATCCGCACCTTTGGGGAGACCAAGATGTCCAATGCTACG
Synthetic  ATGAAGATCGCAGCTTTCAACATCCGCACCTTCGGTGAAACCAAAATGTCCAACGCTACT
           ****** ***** ***************** ** ** ***** ******** *****
Bovine     CTCGCCAGCTACATTGTTCGGATCGTGCGTCGTTACGACATCGTCCTCATCCAGGACGTC
Synthetic  CTGGCAAGCTACATTGTTCGTATCGTGCGTCGTTACGACATCGTTCTGATCCAGGAGGTT
           ** ** ******************** ******************** ** **********
Bovine     AGAGACAGCCACCTGGTGGCTGTGGGGAAGCTCCTGGACTATCTCAACCAGGATGACCCA
Synthetic  AGGGACAGCCACCTGGTAGCTGTTGGTAAGCTGCTGGACTACCTGAACCAGGATGACCCA
           ** ************** ***** ** ***** ******* ** *****************
Bovine     AACACCTACCACTATGTGGTCAGTGAGCCGCTGGGCCGCAACAGCTACAAGGAGCGCTAC
Synthetic  AACACCTACCACTATGTAGTTAGCGAGCCGCTGGGCCGCAACAGCTACAAAGAGCGCTAC
           ***************** ** ** ************************** *********
Bovine     CTCTTTCTGTTCAGACCCAACAAGGTGTCCGTGCTGGACACCTACCAGTACGACGACGGC
Synthetic  CTGTTTCTGTTCCGTCCGAACAAGGTTTCCGTGCTGGACACCTACCAGTACGACGACGGC
           ** ********* * ** ******** *********************************
Bovine     TGCGAGTCCTGCGGGAACGACAGCTTCAGCCGGGAGCCCGCTGTGGTCAAGTTCTCATCC
Synthetic  TGCGAGTCCTGCGGTAACGACAGCTTCAGCCGTGAGCCGGCTGTGGTTAAGTTCTCTTCC
           ************** ***************** ***** ******* ******** ***
Bovine     CACTCCACCAAGGTCAAGGAATTTGCCATTGTTGCCCTGCACTCGGCCCCATCGGACGCA
Synthetic  CACTCCACCAAGGTAAAGGAATTTGCTATTGTTGCTCTGCACTCTGCACCATCCGACGCA
           ************** *********** ******** ******** ** ***** ******
Bovine     GTGGCTGAGATTAATTCTCTACGATGTCTACCTGGATGTCCAGCAGAAGTGGCACTTG
Synthetic  GTAGCTGAGATTAACTCTCTGTACGATGTTTACCTGGATGTTCAGCAGAAGTGGCACCTG
           ** *********** ***** ******** *********** *************** **
Bovine     AACGATGTCATGTTGATGGGCGATTTCAATGCTGACTGCAGCTACGTGACCTCCTCGCAG
Synthetic  AACGATGTAATGCTGATGGGCGATTTCAACGCTGACTGCAGCTACGTAACCTCCTCTCAG
           ******** *** **************** *************** ******** ***
Bovine     TGGTCATCCATCCGCCTGCGTACGAGCTCCACCTTCCAGTGGCTGATTCCTGACAGTGCC
Synthetic  TGGTCTTCCATCCGCCTGCGTACCAGCTCCACCTTCCAGTGGCTGATTCCGGACAGCGCT
           ***** ***************** ************************** ***** **
Bovine     GACACCACGGCTACGTCCACGAACTGCGCCTATGACAGGATCGTGGTCGCAGGGTCTCTG
Synthetic  GACACCACTGCTACTTCCACCAACTGCGCGTATGACCGTATCGTGGTTGCAGGTTCTCTG
           ******** ***** ***** ******** ****** * ******** ***** ******
Bovine     CTCCAGAGTTCTGTGGTTCCTGGCTCGGCCGCTCCCTTTGACTTCCAAGCTGCATACGGA
Synthetic  CTGCAGAGCTCTGTGGTTCCGGGCTCTGCAGCTCCGTTTGACTTCCAAGCTGCATACGGT
           ** ***** *********** ***** ** ***** ************************
Bovine     CTGAGCAATGAGATGGCCCTGGCCATCAGTGACCATTACCCGGTGGAGGTGACGCTGACA
Synthetic  CTGAGCAACGAGATGGCTCTGGCAATCAGCGACCATTACCCGGTTGAGGTGACCCTGACT
           ******** ******** ***** ***** ***************** ******** ****

Bovine     TAA
Synthetic  TAA
           ***
```

Sequence Identity=89.8%

E13R;N74K DNase I

Wild-type DNase I

SEQUENCE LISTING

```
<160> NUMBER OF SEQ ID NOS: 21

<210> SEQ ID NO 1
<211> LENGTH: 783
<212> TYPE: DNA
<213> ORGANISM: Artificial Sequence
<220> FEATURE:
<223> OTHER INFORMATION: Description of Artificial Sequence: optimized
      synthetic oligonucleotide
<220> FEATURE:
<221> NAME/KEY: CDS
<222> LOCATION: (1)..(783)
<223> OTHER INFORMATION: Bovine amino acid sequence optimized for
      expression in yeast

<400> SEQUENCE: 1 atg aag atc gca gct ttc aac atc cgc acc ttc ggt gaa acc aaa atg      48
Met Lys Ile Ala Ala Phe Asn Ile Arg Thr Phe Gly Glu Thr Lys Met
1               5                   10                  15 tcc aac gct act ctg gca agc tac att gtt cgt atc gtg cgt cgt tac      96
Ser Asn Ala Thr Leu Ala Ser Tyr Ile Val Arg Ile Val Arg Arg Tyr
                20                  25                  30 gac atc gtt ctg atc cag gag gtt agg gac agc cac ctg gta gct gtt     144
Asp Ile Val Leu Ile Gln Glu Val Arg Asp Ser His Leu Val Ala Val
            35                  40                  45 ggt aag ctg ctg gac tac ctg aac cag gat gac cca aac acc tac cac     192
Gly Lys Leu Leu Asp Tyr Leu Asn Gln Asp Asp Pro Asn Thr Tyr His
        50                  55                  60 tat gta gtt agc gag ccg ctg ggc cgc aac agc tac aaa gag cgc tac     240
Tyr Val Val Ser Glu Pro Leu Gly Arg Asn Ser Tyr Lys Glu Arg Tyr
65                  70                  75                  80 ctg ttt ctg ttc cgt ccg aac aag gtt tcc gtg ctg gac acc tac cag     288
Leu Phe Leu Phe Arg Pro Asn Lys Val Ser Val Leu Asp Thr Tyr Gln
                85                  90                  95 tac gac gac ggc tgc gag tcc tgc ggt aac gac agc ttc agc cgt gag     336
Tyr Asp Asp Gly Cys Glu Ser Cys Gly Asn Asp Ser Phe Ser Arg Glu
                100                 105                 110 ccg gct gtg gtt aag ttc tct tcc cac tcc acc aag gta aag gaa ttt     384
Pro Ala Val Val Lys Phe Ser Ser His Ser Thr Lys Val Lys Glu Phe
            115                 120                 125 gct att gtt gct ctg cac tct gca cca tcc gac gca gta gct gag att     432
Ala Ile Val Ala Leu His Ser Ala Pro Ser Asp Ala Val Ala Glu Ile
        130                 135                 140 aac tct ctg tac gat gtt tac ctg gat gtt cag cag aag tgg cac ctg     480
Asn Ser Leu Tyr Asp Val Tyr Leu Asp Val Gln Gln Lys Trp His Leu
145                 150                 155                 160 aac gat gta atg ctg atg ggc gat ttc aac gct gac tgc agc tac gta     528
Asn Asp Val Met Leu Met Gly Asp Phe Asn Ala Asp Cys Ser Tyr Val
                165                 170                 175 acc tcc tct cag tgg tct tcc atc cgc ctg cgt acc agc tcc acc ttc     576
Thr Ser Ser Gln Trp Ser Ser Ile Arg Leu Arg Thr Ser Ser Thr Phe
                180                 185                 190 cag tgg ctg att ccg gac agc gct gac acc act gct act tcc acc aac     624
Gln Trp Leu Ile Pro Asp Ser Ala Asp Thr Thr Ala Thr Ser Thr Asn
            195                 200                 205 tgc gcg tat gac cgt atc gtg gtt gca ggt tct ctg ctg cag agc tct     672
```

-continued

```
Cys Ala Tyr Asp Arg Ile Val Val Ala Gly Ser Leu Leu Gln Ser Ser
    210                 215                 220 gtg gtt ccg ggc tct gca gct ccg ttt gac ttc caa gct gca tac ggt      720
Val Val Pro Gly Ser Ala Ala Pro Phe Asp Phe Gln Ala Ala Tyr Gly
225                 230                 235                 240 ctg agc aac gag atg gct ctg gca atc agc gac cat tac ccg gtt gag      768
Leu Ser Asn Glu Met Ala Leu Ala Ile Ser Asp His Tyr Pro Val Glu
                245                 250                 255 gtg acc ctg act taa                                                  783
Val Thr Leu Thr
        260

<210> SEQ ID NO 2
<211> LENGTH: 260
<212> TYPE: PRT
<213> ORGANISM: Artificial Sequence
<220> FEATURE:
<223> OTHER INFORMATION: Description of Artificial Sequence: optimized
      synthetic amino acid sequence

<400> SEQUENCE: 2

Met Lys Ile Ala Ala Phe Asn Ile Arg Thr Phe Gly Glu Thr Lys Met
1               5                   10                  15

Ser Asn Ala Thr Leu Ala Ser Tyr Ile Val Arg Ile Val Arg Arg Tyr
            20                  25                  30

Asp Ile Val Leu Ile Gln Glu Val Arg Asp Ser His Leu Val Ala Val
        35                  40                  45

Gly Lys Leu Leu Asp Tyr Leu Asn Gln Asp Asp Pro Asn Thr Tyr His
    50                  55                  60

Tyr Val Val Ser Glu Pro Leu Gly Arg Asn Ser Tyr Lys Glu Arg Tyr
65                  70                  75                  80

Leu Phe Leu Phe Arg Pro Asn Lys Val Ser Val Leu Asp Thr Tyr Gln
                85                  90                  95

Tyr Asp Asp Gly Cys Glu Ser Cys Gly Asn Asp Ser Phe Ser Arg Glu
            100                 105                 110

Pro Ala Val Val Lys Phe Ser Ser His Ser Thr Lys Val Lys Glu Phe
        115                 120                 125

Ala Ile Val Ala Leu His Ser Ala Pro Ser Asp Ala Val Ala Glu Ile
    130                 135                 140

Asn Ser Leu Tyr Asp Val Tyr Leu Asp Val Gln Gln Lys Trp His Leu
145                 150                 155                 160

Asn Asp Val Met Leu Met Gly Asp Phe Asn Ala Asp Cys Ser Tyr Val
                165                 170                 175

Thr Ser Ser Gln Trp Ser Ser Ile Arg Leu Arg Thr Ser Ser Thr Phe
            180                 185                 190

Gln Trp Leu Ile Pro Asp Ser Ala Asp Thr Thr Ala Thr Ser Thr Asn
        195                 200                 205

Cys Ala Tyr Asp Arg Ile Val Val Ala Gly Ser Leu Leu Gln Ser Ser
    210                 215                 220

Val Val Pro Gly Ser Ala Ala Pro Phe Asp Phe Gln Ala Ala Tyr Gly
225                 230                 235                 240

Leu Ser Asn Glu Met Ala Leu Ala Ile Ser Asp His Tyr Pro Val Glu
                245                 250                 255

Val Thr Leu Thr
        260

<210> SEQ ID NO 3
```

```
<211> LENGTH: 876
<212> TYPE: DNA
<213> ORGANISM: Artificial Sequence
<220> FEATURE:
<223> OTHER INFORMATION: Bovine sequence optimized for expression in
      yeast
<220> FEATURE:
<221> NAME/KEY: misc_feature
<223> OTHER INFORMATION: Description of Artificial Sequence: synthetic
      oligonucleotide
<220> FEATURE:
<221> NAME/KEY: CDS
<222> LOCATION: (1)..(876)

<400> SEQUENCE: 3 atg aaa tac ctg ctg ccg acc gct gct gct ggt ctg ctg ctc ctc gct      48
Met Lys Tyr Leu Leu Pro Thr Ala Ala Ala Gly Leu Leu Leu Leu Ala
1               5                   10                  15 gcc cag ccg gcg atg gcc atg gat atc gga att aat tcg gat cca atg      96
Ala Gln Pro Ala Met Ala Met Asp Ile Gly Ile Asn Ser Asp Pro Met
            20                  25                  30 aag atc gca gct ttc aac atc cgc acc ttc ggt gaa acc aaa atg tcc     144
Lys Ile Ala Ala Phe Asn Ile Arg Thr Phe Gly Glu Thr Lys Met Ser
        35                  40                  45 aac gct act ctg gca agc tac att gtt cgt atc gtg cgt cgt tac gac     192
Asn Ala Thr Leu Ala Ser Tyr Ile Val Arg Ile Val Arg Arg Tyr Asp
    50                  55                  60 atc gtt ctg atc cag gag gtt agg gac agc cac ctg gta gct gtt ggt     240
Ile Val Leu Ile Gln Glu Val Arg Asp Ser His Leu Val Ala Val Gly
65                  70                  75                  80 aag ctg ctg gac tac ctg aac cag gat gac cca aac acc tac cac tat     288
Lys Leu Leu Asp Tyr Leu Asn Gln Asp Asp Pro Asn Thr Tyr His Tyr
                85                  90                  95 gta gtt agc gag ccg ctg ggc cgc aac agc tac aaa gag cgc tac ctg     336
Val Val Ser Glu Pro Leu Gly Arg Asn Ser Tyr Lys Glu Arg Tyr Leu
            100                 105                 110 ttt ctg ttc cgt ccg aac aag gtt tcc gtg ctg gac acc tac cag tac     384
Phe Leu Phe Arg Pro Asn Lys Val Ser Val Leu Asp Thr Tyr Gln Tyr
        115                 120                 125 gac gac ggc tgc gag tcc tgc ggt aac gac agc ttc agc cgt gag ccg     432
Asp Asp Gly Cys Glu Ser Cys Gly Asn Asp Ser Phe Ser Arg Glu Pro
    130                 135                 140 gct gtg gtt aag ttc tct tcc cac tcc acc aag gta aag gaa ttt gct     480
Ala Val Val Lys Phe Ser Ser His Ser Thr Lys Val Lys Glu Phe Ala
145                 150                 155                 160 att gtt gct ctg cac tct gca cca tcc gac gca gta gct gag att aac     528
Ile Val Ala Leu His Ser Ala Pro Ser Asp Ala Val Ala Glu Ile Asn
                165                 170                 175 tct ctg tac gat gtt tac ctg gat gtt cag cag aag tgg cac ctg aac     576
Ser Leu Tyr Asp Val Tyr Leu Asp Val Gln Gln Lys Trp His Leu Asn
            180                 185                 190 gat gta atg ctg atg ggc gat ttc aac gct gac tgc agc tac gta acc     624
Asp Val Met Leu Met Gly Asp Phe Asn Ala Asp Cys Ser Tyr Val Thr
        195                 200                 205 tcc tct cag tgg tct tcc atc cgc ctg cgt acc agc tcc acc ttc cag     672
Ser Ser Gln Trp Ser Ser Ile Arg Leu Arg Thr Ser Ser Thr Phe Gln
    210                 215                 220 tgg ctg att ccg gac agc gct gac acc act gct act tcc acc aac tgc     720
Trp Leu Ile Pro Asp Ser Ala Asp Thr Thr Ala Thr Ser Thr Asn Cys
225                 230                 235                 240 gcg tat gac cgt atc gtg gtt gca ggt tct ctg ctg cag agc tct gtg     768
Ala Tyr Asp Arg Ile Val Val Ala Gly Ser Leu Leu Gln Ser Ser Val
                245                 250                 255
```

```
gtt ccg ggc tct gca gct ccg ttt gac ttc caa gct gca tac ggt ctg      816
Val Pro Gly Ser Ala Ala Pro Phe Asp Phe Gln Ala Ala Tyr Gly Leu
        260                 265                 270 agc aac gag atg gct ctg gca atc agc gac cat tac ccg gtt gag gtg      864
Ser Asn Glu Met Ala Leu Ala Ile Ser Asp His Tyr Pro Val Glu Val
            275                 280                 285 acc ctg act taa                                                      876
Thr Leu Thr
    290

<210> SEQ ID NO 4
<211> LENGTH: 291
<212> TYPE: PRT
<213> ORGANISM: Artificial Sequence
<220> FEATURE:
<223> OTHER INFORMATION: Bovine sequence optimized for expression in
      yeast

<400> SEQUENCE: 4
```

Met Lys Tyr Leu Leu Pro Thr Ala Ala Ala Gly Leu Leu Leu Leu Ala
1               5                   10                  15

Ala Gln Pro Ala Met Ala Met Asp Ile Gly Ile Asn Ser Asp Pro Met
            20                  25                  30

Lys Ile Ala Ala Phe Asn Ile Arg Thr Phe Gly Glu Thr Lys Met Ser
        35                  40                  45

Asn Ala Thr Leu Ala Ser Tyr Ile Val Arg Ile Val Arg Arg Tyr Asp
    50                  55                  60

Ile Val Leu Ile Gln Glu Val Arg Asp Ser His Leu Val Ala Val Gly
65                  70                  75                  80

Lys Leu Leu Asp Tyr Leu Asn Gln Asp Pro Asn Thr Tyr His Tyr
                85                  90                  95

Val Val Ser Glu Pro Leu Gly Arg Asn Ser Tyr Lys Glu Arg Tyr Leu
            100                 105                 110

Phe Leu Phe Arg Pro Asn Lys Val Ser Val Leu Asp Thr Tyr Gln Tyr
        115                 120                 125

Asp Asp Gly Cys Glu Ser Cys Gly Asn Asp Ser Phe Ser Arg Glu Pro
    130                 135                 140

Ala Val Val Lys Phe Ser Ser His Ser Thr Lys Val Lys Glu Phe Ala
145                 150                 155                 160

Ile Val Ala Leu His Ser Ala Pro Ser Asp Ala Val Ala Glu Ile Asn
                165                 170                 175

Ser Leu Tyr Asp Val Tyr Leu Asp Val Gln Gln Lys Trp His Leu Asn
            180                 185                 190

Asp Val Met Leu Met Gly Asp Phe Asn Ala Asp Cys Ser Tyr Val Thr
        195                 200                 205

Ser Ser Gln Trp Ser Ser Ile Arg Leu Arg Thr Ser Ser Thr Phe Gln
    210                 215                 220

Trp Leu Ile Pro Asp Ser Ala Asp Thr Thr Ala Thr Ser Thr Asn Cys
225                 230                 235                 240

Ala Tyr Asp Arg Ile Val Val Ala Gly Ser Leu Leu Gln Ser Ser Val
                245                 250                 255

Val Pro Gly Ser Ala Ala Pro Phe Asp Phe Gln Ala Ala Tyr Gly Leu
            260                 265                 270

Ser Asn Glu Met Ala Leu Ala Ile Ser Asp His Tyr Pro Val Glu Val
        275                 280                 285

Thr Leu Thr
    290

```
<210> SEQ ID NO 5
<211> LENGTH: 282
<212> TYPE: PRT
<213> ORGANISM: Bovine

<400> SEQUENCE: 5

Met Arg Gly Thr Arg Leu Met Gly Leu Leu Ala Leu Ala Gly Leu
1               5                   10                  15

Leu Gln Leu Gly Leu Ser Leu Lys Ile Ala Ala Phe Asn Ile Arg Thr
            20                  25                  30

Phe Gly Glu Thr Lys Met Ser Asn Ala Thr Leu Ala Ser Tyr Ile Val
        35                  40                  45

Arg Ile Val Arg Arg Tyr Asp Ile Val Leu Ile Gln Glu Val Arg Asp
    50                  55                  60

Ser His Leu Val Ala Val Gly Lys Leu Leu Asp Tyr Leu Asn Gln Asp
65                  70                  75                  80

Asp Pro Asn Thr Tyr His Tyr Val Val Ser Glu Pro Leu Gly Arg Asn
                85                  90                  95

Ser Tyr Lys Glu Arg Tyr Leu Phe Leu Phe Arg Pro Asn Lys Val Ser
            100                 105                 110

Val Leu Asp Thr Tyr Gln Tyr Asp Asp Gly Cys Glu Ser Cys Gly Asn
        115                 120                 125

Asp Ser Phe Ser Arg Glu Pro Ala Val Val Lys Phe Ser Ser His Ser
    130                 135                 140

Thr Lys Val Lys Glu Phe Ala Ile Val Ala Leu His Ser Ala Pro Ser
145                 150                 155                 160

Asp Ala Val Ala Glu Ile Asn Ser Leu Tyr Asp Val Tyr Leu Asp Val
                165                 170                 175

Gln Gln Lys Trp His Leu Asn Asp Val Met Leu Met Gly Asp Phe Asn
            180                 185                 190

Ala Asp Cys Ser Tyr Val Thr Ser Ser Gln Trp Ser Ser Ile Arg Leu
        195                 200                 205

Arg Thr Ser Ser Thr Phe Gln Trp Leu Ile Pro Asp Ser Ala Asp Thr
    210                 215                 220

Thr Ala Thr Ser Thr Asn Cys Ala Tyr Asp Arg Ile Val Val Ala Gly
225                 230                 235                 240

Ser Leu Leu Gln Ser Ser Val Val Pro Gly Ser Ala Ala Pro Phe Asp
                245                 250                 255

Phe Gln Ala Ala Tyr Gly Leu Ser Asn Glu Met Ala Leu Ala Ile Ser
            260                 265                 270

Asp His Tyr Pro Val Glu Val Thr Leu Thr
        275                 280

<210> SEQ ID NO 6
<211> LENGTH: 360
<212> TYPE: PRT
<213> ORGANISM: Ovine sp.

<400> SEQUENCE: 6

Leu Lys Ile Ala Ala Phe Asn Ile Arg Thr Phe Gly Glu Thr Lys Met
1               5                   10                  15

Ser Asn Ala Thr Leu Ser Ser Tyr Ile Val Arg Ile Leu Arg Arg Tyr
            20                  25                  30

Asp Ile Ala Leu Ile Glu Gln Val Arg Asp Ser His Leu Val Ala Val
        35                  40                  45
```

```
Gly Lys Leu Leu Asp Asp Leu Asn Gln Asp Asp Pro Asn Ser Tyr His
    50                  55                  60
Tyr Val Val Ser Glu Pro Leu Gly Arg Asn Ser Tyr Lys Glu Arg Tyr
65                  70                  75                  80
Leu Phe Val Phe Arg Pro Asn Lys Val Ser Val Leu Asp Thr Tyr Gln
                85                  90                  95
Tyr Asp Asp Gly Cys Glu Ser Cys Gly Asn Asp Ser Phe Ser Arg Glu
            100                 105                 110
Pro Ala Val Val Lys Phe Ser Ser Pro Ser Thr Lys Val Lys Ala Phe
        115                 120                 125
Ala Ile Val Pro Leu His Ser Ala Pro Ser Asp Ala Val Ala Glu Ile
    130                 135                 140
Asn Ser Leu Tyr Asp Val Tyr Leu Asp Val Gln Gln Lys Trp Asp Leu
145                 150                 155                 160
Asn Asp Ile Met Leu Met Gly Asp Phe Asn Ala Asp Cys Ser Tyr Val
                165                 170                 175
Ala Phe Ala Ile Val Pro Leu His Ser Ala Pro Ser Asp Ala Val Ala
            180                 185                 190
Glu Ile Asn Ser Leu Tyr Asp Val Tyr Leu Asp Val Gln Gln Lys Trp
        195                 200                 205
Asp Leu Asn Asp Ile Met Leu Met Gly Asp Phe Asn Ala Asp Cys Ser
    210                 215                 220
Tyr Val Ala Phe Ala Ile Val Pro Leu His Ser Ala Pro Ser Asp Ala
225                 230                 235                 240
Val Ala Glu Ile Asn Ser Leu Tyr Asp Val Tyr Leu Asp Val Gln Gln
                245                 250                 255
Lys Trp Asp Leu Asn Asp Ile Met Leu Met Gly Asp Phe Asn Ala Asp
            260                 265                 270
Cys Ser Tyr Val Thr Ser Ser Gln Trp Ser Ser Ile Arg Leu Arg Thr
        275                 280                 285
Ser Ser Thr Phe Gln Trp Leu Ile Pro Asp Ser Ala Asp Thr Thr Ala
    290                 295                 300
Thr Ser Thr Asn Cys Ala Tyr Asp Arg Ile Val Val Ala Gly Ser Leu
305                 310                 315                 320
Leu Gln Ser Ser Val Val Gly Pro Ser Ala Val Pro Phe Asp Phe Gln
                325                 330                 335
Ala Ala Tyr Gly Leu Ser Asn Glu Met Ala Leu Ala Ile Ser Asp His
            340                 345                 350
Tyr Pro Val Glu Val Thr Leu Thr
        355                 360

<210> SEQ ID NO 7
<211> LENGTH: 262
<212> TYPE: PRT
<213> ORGANISM: Porcine sp.

<400> SEQUENCE: 7

Leu Arg Ile Ala Ala Phe Asn Ile Arg Thr Phe Gly Glu Thr Lys Met
1               5                   10                  15
Ser Asn Ala Thr Leu Ser Asn Tyr Ile Val Arg Ile Leu Ser Arg Tyr
                20                  25                  30
Asp Ile Ala Leu Ile Gln Glu Val Arg Asp Ser His Leu Thr Ala Val
            35                  40                  45
Gly Lys Leu Leu Asn Glu Leu Asn Gln Asp Asp Pro Asn Asn Tyr His
```

```
            50                  55                  60
His Val Val Ser Glu Pro Leu Gly Arg Ser Thr Tyr Lys Glu Arg Tyr
 65                  70                  75                  80

Leu Phe Val Phe Arg Pro Asn Gln Val Ser Val Leu Asp Ser Tyr Leu
                 85                  90                  95

Tyr Asp Asp Gly Cys Glu Pro Cys Gly Asn Asp Thr Phe Asn Arg Glu
             100                 105                 110

Pro Ser Val Val Lys Phe Ser Ser Pro Phe Thr Gln Val Lys Glu Phe
         115                 120                 125

Ala Ile Val Pro Leu His Ala Ala Pro Ser Asp Ala Ala Glu Ile
    130                 135                 140

Asn Ser Leu Tyr Asp Val Tyr Leu Asn Val Arg Gln Lys Trp Asp Leu
145                 150                 155                 160

Gln Asp Ile Met Leu Met Gly Asp Phe Asn Ala Gly Cys Ser Tyr Val
                165                 170                 175

Thr Thr Ser His Trp Ser Ser Ile Arg Leu Arg Glu Ser Pro Pro Phe
            180                 185                 190

Gln Trp Leu Ile Pro Asp Thr Ala Asp Thr Thr Val Ser Ser His Thr
        195                 200                 205

Cys Ala Tyr Asp Arg Ile Val Val Ala Gly Pro Leu Leu Gln Arg Ala
    210                 215                 220

Val Val Pro Asp Ser Ala Ala Pro Phe Asp Phe Gln Ala Ala Phe Gly
225                 230                 235                 240

Leu Ser Gln Glu Thr Ala Leu Ala Ile Ser Asp His Tyr Pro Val Glu
                245                 250                 255

Val Thr Leu Lys Arg Ala
            260

<210> SEQ ID NO 8
<211> LENGTH: 284
<212> TYPE: PRT
<213> ORGANISM: Rattus sp.

<400> SEQUENCE: 8

Met Arg Tyr Thr Gly Leu Met Gly Ile Leu Leu Thr Leu Val Asn Leu
 1               5                  10                  15

Leu Gln Leu Ala Ala Thr Leu Arg Ile Ala Ala Phe Asn Ile Arg Thr
                20                  25                  30

Phe Gly Asp Thr Lys Met Ser Asn Ala Thr Leu Ser Ser Tyr Ile Val
             35                  40                  45

Lys Ile Leu Ser Arg Tyr Asp Ile Ala Val Val Gln Glu Val Arg Asp
 50                  55                  60

Thr His Leu Val Ala Val Gly Lys Leu Leu Asp Glu Leu Asn Arg Asp
 65                  70                  75                  80

Ile Pro Asp Asn Tyr Arg Tyr Ile Ile Ser Glu Pro Leu Gly Arg Lys
                 85                  90                  95

Ser Tyr Lys Glu Gln Tyr Leu Phe Val Tyr Arg Pro Ser Gln Val Ser
             100                 105                 110

Val Leu Asp Ser Tyr His Tyr Asp Asp Gly Cys Glu Pro Cys Gly Asn
         115                 120                 125

Asp Thr Phe Ser Arg Glu Pro Ala Ile Val Lys Phe Phe Ser Pro Tyr
    130                 135                 140

Thr Glu Val Arg Glu Phe Ala Ile Val Pro Leu His Ser Ala Pro Thr
145                 150                 155                 160
```

```
Glu Ala Val Ser Glu Ile Asp Ala Leu Tyr Asp Val Tyr Leu Asp Val
                165                 170                 175

Arg Gln Lys Trp Gly Leu Glu Asp Ile Met Phe Met Gly Asp Phe Asn
            180                 185                 190

Ala Gly Cys Ser Tyr Val Thr Ser Ser Gln Trp Ser Ser Ile Arg Leu
            195                 200                 205

Arg Thr Ser Pro Ile Phe Gln Trp Leu Ile Pro Asp Ser Ala Asp Thr
210                 215                 220

Thr Ala Thr Ser Thr His Cys Ala Tyr Asp Arg Ile Val Val Ala Gly
225                 230                 235                 240

Ala Leu Leu Gln Ala Ala Val Pro Ser Ala Val Pro Phe Asp
                245                 250                 255

Phe Gln Ala Glu Tyr Arg Leu Thr Asn Gln Met Ala Glu Ala Ile Ser
            260                 265                 270

Asp His Tyr Pro Val Glu Val Thr Leu Arg Lys Thr
            275                 280
```

<210> SEQ ID NO 9
<211> LENGTH: 284
<212> TYPE: PRT
<213> ORGANISM: Mus musculus

<400> SEQUENCE: 9

```
Met Arg Tyr Thr Gly Leu Met Gly Thr Leu Leu Thr Leu Val Asn Leu
1               5                   10                  15

Leu Gln Leu Ala Gly Thr Leu Arg Ile Ala Ala Phe Asn Ile Arg Thr
                20                  25                  30

Phe Gly Glu Thr Lys Met Ser Asn Ala Thr Leu Ser Val Tyr Phe Val
            35                  40                  45

Lys Ile Leu Ser Arg Tyr Asp Ile Ala Val Ile Gln Glu Val Arg Asp
        50                  55                  60

Ser His Leu Val Ala Val Gly Lys Leu Leu Asp Glu Leu Asn Arg Asp
65                  70                  75                  80

Lys Pro Asp Thr Tyr Arg Tyr Val Val Ser Glu Pro Leu Gly Arg Lys
                85                  90                  95

Ser Tyr Lys Glu Gln Tyr Leu Phe Val Tyr Arg Pro Asp Gln Val Ser
            100                 105                 110

Ile Leu Asp Ser Tyr Gln Tyr Asp Asp Gly Cys Glu Pro Cys Gly Asn
        115                 120                 125

Asp Thr Phe Ser Arg Glu Pro Ala Ile Val Lys Phe Phe Ser Pro Tyr
    130                 135                 140

Thr Glu Val Gln Glu Phe Ala Ile Val Pro Leu His Ala Ala Pro Thr
145                 150                 155                 160

Glu Ala Val Ser Glu Ile Asp Ala Leu Tyr Asp Val Tyr Leu Asp Val
                165                 170                 175

Trp Gln Lys Trp Gly Leu Glu Asp Ile Met Phe Met Gly Asp Phe Asn
            180                 185                 190

Ala Gly Cys Ser Tyr Val Thr Ser Ser Gln Trp Ser Ser Ile Arg Leu
            195                 200                 205

Arg Thr Ser Pro Ile Phe Gln Trp Leu Ile Pro Asp Ser Ala Asp Thr
210                 215                 220

Thr Val Thr Ser Thr His Cys Ala Tyr Asp Arg Ile Val Val Ala Gly
225                 230                 235                 240

Ala Leu Leu Gln Ala Ala Val Pro Asn Ser Ala Val Pro Phe Asp
                245                 250                 255
```

```
Phe Gln Ala Glu Tyr Gly Leu Ser Asn Gln Leu Ala Glu Ala Ile Ser
            260                 265                 270

Asp His Tyr Pro Val Glu Val Thr Leu Arg Lys Ile
            275                 280

<210> SEQ ID NO 10
<211> LENGTH: 282
<212> TYPE: PRT
<213> ORGANISM: Homo sapiens

<400> SEQUENCE: 10

Met Arg Gly Met Lys Leu Leu Gly Ala Leu Ala Leu Ala Leu Ala Leu
1               5                   10                  15

Leu Gln Gly Ala Val Ser Leu Lys Ile Ala Ala Phe Asn Ile Gln Thr
            20                  25                  30

Phe Gly Glu Thr Lys Met Ser Asn Ala Thr Leu Val Ser Tyr Ile Val
            35                  40                  45

Gln Ile Leu Ser Arg Tyr Asp Ile Ala Leu Val Gln Glu Val Arg Asp
        50                  55                  60

Ser His Leu Thr Ala Val Gly Lys Leu Leu Asp Asn Leu Asn Gln Asp
65                  70                  75                  80

Ala Pro Asp Thr Tyr His Tyr Val Val Ser Glu Pro Leu Gly Arg Asn
                85                  90                  95

Ser Tyr Lys Glu Arg Tyr Leu Phe Val Tyr Arg Pro Asp Gln Val Ser
            100                 105                 110

Ala Val Asp Ser Tyr Tyr Tyr Asp Asp Gly Cys Glu Pro Cys Gly Asn
            115                 120                 125

Asp Thr Phe Asn Arg Glu Pro Ala Ile Val Arg Phe Phe Ser Arg Phe
    130                 135                 140

Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
                165                 170                 175

Gln Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ser Ile Arg Leu
            195                 200                 205

Trp Thr Ser Pro Thr Phe Gln Trp Leu Ile Pro Asp Ser Ala Asp Thr
    210                 215                 220

Thr Ala Thr Pro Thr His Cys Ala Tyr Asp Arg Ile Val Val Ala Gly
225                 230                 235                 240

Met Leu Leu Arg Gly Ala Val Val Pro Asp Ser Ala Leu Pro Phe Asn
                245                 250                 255

Phe Gln Ala Ala Tyr Gly Leu Ser Asp Gln Leu Ala Gln Ala Ile Ser
            260                 265                 270

Asp His Tyr Pro Val Glu Val Met Leu Lys
            275                 280

<210> SEQ ID NO 11
<211> LENGTH: 281
<212> TYPE: PRT
<213> ORGANISM: Rabbit

<400> SEQUENCE: 11

Met Arg Ser Glu Met Leu Thr Ala Leu Leu Thr Leu Ala Val Leu Leu
1               5                   10                  15
```

Gln Val Ala Gly Ser Leu Lys Ile Ala Ala Phe Asn Ile Arg Ser Phe
            20                  25                  30

Gly Glu Thr Lys Met Ser Asn Ala Thr Leu Thr Ser Tyr Ile Val Arg
            35                  40                  45

Ile Leu Gln Arg Tyr Asp Ile Ala Leu Ile Gln Glu Val Arg Asp Ser
            50                  55                  60

His Leu Thr Ala Val Gly Lys Leu Leu Asp Lys Leu Asn Glu Lys Ala
 65                  70                  75                  80

Ala Asp Thr Tyr Arg Phe Val Ala Ser Glu Pro Leu Gly Arg Arg Thr
                85                  90                  95

Tyr Lys Glu Arg Tyr Leu Phe Val Tyr Arg Pro Asp Gln Val Ser Val
            100                 105                 110

Leu Asp Ser Tyr Tyr Asp Asp Gly Cys Glu Pro Cys Gly Thr Asp
            115                 120                 125

Thr Phe Ser Arg Glu Pro Ala Val Val Arg Phe Ser Ser Pro Ser Thr
            130                 135                 140

Lys Val Arg Glu Phe Ala Ile Val Pro Leu His Ser Ala Pro Glu Asp
145                 150                 155                 160

Ala Val Ala Glu Ile Asp Ala Leu Tyr Asp Val Tyr Leu Asp Val Gln
                165                 170                 175

Lys Lys Trp Gly Leu Gln Asp Val Met Leu Met Gly Asp Phe Asn Ala
            180                 185                 190

Asp Tyr Ser Tyr Val Thr Ser Ser Gln Trp Ser Ser Ile Arg Leu Arg
            195                 200                 205

Thr Asn Pro Ala Phe Lys Trp Leu Ile Pro Asp Thr Ala Asp Thr Thr
            210                 215                 220

Ala Thr Ser Thr Asn Cys Ala Tyr Asp Arg Ile Val Val Ala Gly Pro
225                 230                 235                 240

Leu Leu Gln Asp Ala Val Val Pro Asn Ser Ala Ala Pro Phe Asn Phe
                245                 250                 255

Gln Ala Ala Tyr Gly Leu Ser Asn Gln Leu Ala Gln Ala Ile Ser Asp
            260                 265                 270

His Tyr Pro Val Glu Val Thr Leu Ala
            275                 280

<210> SEQ ID NO 12
<211> LENGTH: 305
<212> TYPE: PRT
<213> ORGANISM: LS sp.

<400> SEQUENCE: 12

Met Ser Arg Glu Leu Ala Pro Leu Leu Leu Leu Leu Ser Ile His
 1               5                  10                  15

Ser Ala Leu Ala Met Arg Ile Cys Ser Phe Asn Val Arg Ser Phe Gly
            20                  25                  30

Glu Ser Lys Gln Glu Asp Lys Asn Ala Met Asp Val Ile Val Lys Val
            35                  40                  45

Ile Lys Arg Cys Asp Ile Ile Leu Val Met Glu Ile Lys Asp Ser Asn
            50                  55                  60

Asn Arg Ile Cys Pro Ile Leu Met Glu Lys Leu Asn Arg Asn Ser Arg
 65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser

```
                100             105             110
Val Lys Arg Ser Tyr His Tyr His Asp Tyr Gln Asp Gly Asp Ala Asp
        115                 120                 125
Val Phe Ser Arg Glu Pro Phe Val Trp Phe Gln Ser Pro His Thr
130                 135                 140
Ala Val Lys Asp Phe Val Ile Ile Pro Leu His Thr Thr Pro Glu Thr
145                 150                 155                 160
Ser Val Lys Glu Ile Asp Glu Leu Val Glu Val Tyr Thr Asp Val Lys
                165                 170                 175
His Arg Trp Lys Ala Glu Asn Phe Ile Phe Met Gly Asp Phe Asn Ala
                180                 185                 190
Gly Cys Ser Tyr Val Pro Lys Lys Ala Trp Lys Asn Ile Arg Leu Arg
                195                 200                 205
Thr Asp Pro Arg Phe Val Trp Leu Ile Gly Asp Gln Glu Asp Thr Thr
        210                 215                 220
Val Lys Lys Ser Thr Asn Cys Ala Tyr Asp Arg Ile Val Leu Arg Gly
225                 230                 235                 240
Gln Glu Ile Val Ser Ser Val Pro Lys Ser Asn Ser Val Phe Asp
                245                 250                 255
Phe Gln Lys Ala Tyr Lys Leu Thr Glu Glu Ala Leu Asp Val Ser
            260                 265                 270
Asp His Phe Pro Val Glu Phe Lys Leu Gln Ser Ser Arg Ala Phe Thr
        275                 280                 285
Asn Ser Lys Lys Ser Val Thr Leu Arg Lys Lys Thr Lys Ser Lys Arg
        290                 295                 300
Ser
305

<210> SEQ ID NO 13
<211> LENGTH: 41
<212> TYPE: DNA
<213> ORGANISM: Rattus sp.

<400> SEQUENCE: 13
atccgctcga gaagagactg aagatcgcag ctttcaacat c                41

<210> SEQ ID NO 14
<211> LENGTH: 39
<212> TYPE: DNA
<213> ORGANISM: Rattus sp.

<400> SEQUENCE: 14
ataagaatgc ggccgcttaa gtcagggtca cctcaaccg                  39

<210> SEQ ID NO 15
<211> LENGTH: 41
<212> TYPE: DNA
<213> ORGANISM: Rattus sp.

<400> SEQUENCE: 15
catccgcacc ttcggccgta ccaaaatgtc caacgctact c               41

<210> SEQ ID NO 16
<211> LENGTH: 41
<212> TYPE: DNA
<213> ORGANISM: Rattus sp.

<400> SEQUENCE: 16
```

```
gagtagcgtt ggacattttg gtacggccga aggtgcggat g            41
```

<210> SEQ ID NO 17
<211> LENGTH: 31
<212> TYPE: DNA
<213> ORGANISM: Rattus sp.

<400> SEQUENCE: 17

```
gccgctgggc cgcaagagct acaaagagcg c                       31
```

<210> SEQ ID NO 18
<211> LENGTH: 30
<212> TYPE: DNA
<213> ORGANISM: Rattus sp.

<400> SEQUENCE: 18

```
ctttgtagct cttgcggccg agcggctcgc                         30
```

<210> SEQ ID NO 19
<211> LENGTH: 1046
<212> TYPE: DNA
<213> ORGANISM: Artificial Sequence
<220> FEATURE:
<223> OTHER INFORMATION: Pichia expression vector with synthetic
      DNase I insert
<220> FEATURE:
<221> NAME/KEY: misc_feature
<223> OTHER INFORMATION: Description of Artificial Sequence: synthetic
      oligonucleotide

<400> SEQUENCE: 19

```
atgagatttc cttcaatttt tactgctgtt ttattcgcag catcctccgc attagctgct    60
ccagtcaaca ctacaacaga agatgaaacg gcacaaattc cggctgaagc tgtcatcggt   120
tactcagatt tagaagggga tttcgatgtt gctgttttgc catttccaa cagcacaaat    180
aacgggttat tgtttataaa tactactatt gccagcattg ctgctaaaga agaagggta    240
tctctcgaga agagactgaa gatcgcagct ttcaacatcc gccttcgg tgaaaccaaa     300
atgtccaacg ctactctggc aagctacatt gttcgtatcg tgcgtcgtta cgacatcgtt    360
ctgatccagg aggttaggga cagccacctg gtagctgttg gtaagctgct ggactacctg   420
aaccaggatg acccaaacac ctaccactat gtagttagcg agccgctggg ccgcaacagc   480
tacaaagagc gctacctgtt tctgttccgt ccgaacaagg tttccgtgct ggacacctac   540
cagtacgacg acggctgcga gtcctgcggt aacgacagct tcagccgtga gccggctgtg   600
gttaagttct cttcccactc caccaaggta aaggaatttg ctattgttgc tctgcactct   660
gcaccatccg acgcagtagc tgagattaac tctctgtacg atgtttacct ggatgttcag   720
cagaagtggc acctgaacga tgtaatgctg atgggcgatt caacgctga ctgcagctac    780
gtaacctcct ctcagtggtc ttccatccgc ctgcgtacca gctccacctt ccagtggctg   840
attccggaca gcgctgacac cactgctact tccaccaact gcgcgtatga ccgtatcgtg   900
gttgcaggtt ctctgctgca gagctctgtg gttccgggct ctgcagctcc gttttgacttc   960
caagctgcat acggtctgag caacgagatg gctctggcaa tcagcgacca ttacccggtt  1020
gaggtgaccc tgacttaagc ggccgc                                       1046
```

<210> SEQ ID NO 20
<211> LENGTH: 345
<212> TYPE: PRT
<213> ORGANISM: Artificial Sequence
<220> FEATURE:

<223> OTHER INFORMATION: Artificial sequence: fusion protein
<220> FEATURE:
<221> NAME/KEY: misc_feature
<223> OTHER INFORMATION: Artificial Sequence: alpha mating factor
    leader fusion protein llinked to a synthetic DNase I

<400> SEQUENCE: 20

| Met | Arg | Phe | Pro | Ser | Ile | Phe | Thr | Ala | Val | Leu | Phe | Ala | Ala | Ser | Ser |
|---|---|---|---|---|---|---|---|---|---|---|---|---|---|---|---|
| 1 | | | | 5 | | | | | 10 | | | | | 15 | |

| Ala | Leu | Ala | Ala | Pro | Val | Asn | Thr | Thr | Thr | Glu | Asp | Glu | Thr | Ala | Gln |
|---|---|---|---|---|---|---|---|---|---|---|---|---|---|---|---|
| | | | 20 | | | | | 25 | | | | | 30 | | |

| Ile | Pro | Ala | Glu | Ala | Val | Ile | Gly | Tyr | Ser | Asp | Leu | Glu | Gly | Asp | Phe |
|---|---|---|---|---|---|---|---|---|---|---|---|---|---|---|---|
| | | 35 | | | | | 40 | | | | | 45 | | | |

| Asp | Val | Ala | Val | Leu | Pro | Phe | Ser | Asn | Ser | Thr | Asn | Asn | Gly | Leu | Leu |
|---|---|---|---|---|---|---|---|---|---|---|---|---|---|---|---|
| | 50 | | | | | 55 | | | | | 60 | | | | |

| Phe | Ile | Asn | Thr | Thr | Ile | Ala | Ser | Ile | Ala | Ala | Lys | Glu | Glu | Gly | Val |
|---|---|---|---|---|---|---|---|---|---|---|---|---|---|---|---|
| 65 | | | | | 70 | | | | | 75 | | | | | 80 |

| Ser | Leu | Glu | Lys | Arg | Leu | Lys | Ile | Ala | Ala | Phe | Asn | Ile | Arg | Thr | Phe |
|---|---|---|---|---|---|---|---|---|---|---|---|---|---|---|---|
| | | | | 85 | | | | | 90 | | | | | 95 | |

| Gly | Glu | Thr | Lys | Met | Ser | Asn | Ala | Thr | Leu | Ala | Ser | Tyr | Ile | Val | Arg |
|---|---|---|---|---|---|---|---|---|---|---|---|---|---|---|---|
| | | | 100 | | | | | 105 | | | | | 110 | | |

| Ile | Val | Arg | Arg | Tyr | Asp | Ile | Val | Leu | Ile | Gln | Glu | Val | Arg | Asp | Ser |
|---|---|---|---|---|---|---|---|---|---|---|---|---|---|---|---|
| | | 115 | | | | | 120 | | | | | 125 | | | |

| His | Leu | Val | Ala | Val | Gly | Lys | Leu | Leu | Asp | Tyr | Leu | Asn | Gln | Asp | Asp |
|---|---|---|---|---|---|---|---|---|---|---|---|---|---|---|---|
| | 130 | | | | | 135 | | | | | 140 | | | | |

| Pro | Asn | Thr | Tyr | His | Tyr | Val | Val | Ser | Glu | Pro | Leu | Gly | Arg | Asn | Ser |
|---|---|---|---|---|---|---|---|---|---|---|---|---|---|---|---|
| 145 | | | | | 150 | | | | | 155 | | | | | 160 |

| Tyr | Lys | Glu | Arg | Tyr | Leu | Phe | Leu | Phe | Arg | Pro | Asn | Lys | Val | Ser | Val |
|---|---|---|---|---|---|---|---|---|---|---|---|---|---|---|---|
| | | | | 165 | | | | | 170 | | | | | 175 | |

| Leu | Asp | Thr | Tyr | Gln | Tyr | Asp | Asp | Gly | Cys | Glu | Ser | Cys | Gly | Asn | Asp |
|---|---|---|---|---|---|---|---|---|---|---|---|---|---|---|---|
| | | | 180 | | | | | 185 | | | | | 190 | | |

| Ser | Phe | Ser | Arg | Glu | Pro | Ala | Val | Val | Lys | Phe | Ser | Ser | His | Ser | Thr |
|---|---|---|---|---|---|---|---|---|---|---|---|---|---|---|---|
| | | 195 | | | | | 200 | | | | | 205 | | | |

| Lys | Val | Lys | Glu | Phe | Ala | Ile | Val | Ala | Leu | His | Ser | Ala | Pro | Ser | Asp |
|---|---|---|---|---|---|---|---|---|---|---|---|---|---|---|---|
| 210 | | | | | 215 | | | | | 220 | | | | | |

| Ala | Val | Ala | Glu | Ile | Asn | Ser | Leu | Tyr | Asp | Val | Tyr | Leu | Asp | Val | Gln |
|---|---|---|---|---|---|---|---|---|---|---|---|---|---|---|---|
| 225 | | | | | 230 | | | | | 235 | | | | | 240 |

| Gln | Lys | Trp | His | Leu | Asn | Asp | Val | Met | Leu | Met | Gly | Asp | Phe | Asn | Ala |
|---|---|---|---|---|---|---|---|---|---|---|---|---|---|---|---|
| | | | | 245 | | | | | 250 | | | | | 255 | |

| Asp | Cys | Ser | Tyr | Val | Thr | Ser | Ser | Gln | Trp | Ser | Ser | Ile | Arg | Leu | Arg |
|---|---|---|---|---|---|---|---|---|---|---|---|---|---|---|---|
| | | | 260 | | | | | 265 | | | | | 270 | | |

| Thr | Ser | Ser | Thr | Phe | Gln | Trp | Leu | Ile | Pro | Asp | Ser | Ala | Asp | Thr | Thr |
|---|---|---|---|---|---|---|---|---|---|---|---|---|---|---|---|
| | | 275 | | | | | 280 | | | | | 285 | | | |

| Ala | Thr | Ser | Thr | Asn | Cys | Ala | Tyr | Asp | Arg | Ile | Val | Val | Ala | Gly | Ser |
|---|---|---|---|---|---|---|---|---|---|---|---|---|---|---|---|
| | 290 | | | | | 295 | | | | | 300 | | | | |

| Leu | Leu | Gln | Ser | Ser | Val | Val | Pro | Gly | Ser | Ala | Ala | Pro | Phe | Asp | Phe |
|---|---|---|---|---|---|---|---|---|---|---|---|---|---|---|---|
| 305 | | | | | 310 | | | | | 315 | | | | | 320 |

| Gln | Ala | Ala | Tyr | Gly | Leu | Ser | Asn | Glu | Met | Ala | Leu | Ala | Ile | Ser | Asp |
|---|---|---|---|---|---|---|---|---|---|---|---|---|---|---|---|
| | | | | 325 | | | | | 330 | | | | | 335 | |

| His | Tyr | Pro | Val | Glu | Val | Thr | Leu | Thr |
|---|---|---|---|---|---|---|---|---|
| | | | 340 | | | | | 345 |

<210> SEQ ID NO 21
<211> LENGTH: 783
<212> TYPE: DNA
<213> ORGANISM: Bovine

```
<220> FEATURE:
<221> NAME/KEY: misc_feature
<222> LOCATION: (1)..(783)
<223> OTHER INFORMATION: Description of Sequence: bovine DNase I
      sequence used for comparison

<400> SEQUENCE: 21
ctgaagatag cagccttcaa catccgcacc tttggggaga ccaagatgtc caatgctacg      60
ctcgccagct acattgttcg gatcgtgcgt cgttacgaca tcgtcctcat ccaggaggtc     120
agagacagcc acctggtggc tgtggggaag ctcctggact atctcaacca ggatgaccca     180
aacacctacc actatgtggt cagtgagccg ctgggccgca acagctacaa ggagcgctac     240
ctctttctgt tcagacccaa caaggtgtcc gtgctggaca cctaccagta cgacgacggc     300
tgcgagtcct gcgggaacga cagcttcagc cgggagcccg ctgtggtcaa gttctcatcc     360
cactccacca aggtcaagga atttgccatt gttgccctgc actcggcccc atcggacgca     420
gtggctgaga ttaattctct ctacgatgtc tacctggatg tccagcagaa gtggcacttg     480
aacgatgtca tgttgatggg cgatttcaat gctgactgca gctacgtgac ctcctcgcag     540
tggtcatcca tccgcctgcg tacgagctcc accttccagt ggctgattcc tgacagtgcc     600
gacaccacgg ctacgtccac gaactgcgcc tatgacagga tcgtggtcgc agggtctctg     660
ctccagagtt ctgtggttcc tggctcggcc gctcccttttg acttccaagc tgcatacgga     720
ctgagcaatg agatggccct ggccatcagt gaccattacc cggtggaggt gacgctgaca     780
taa                                                                   783
```

COMPOSITIONS AND METHODS OF USING A SYNTHETIC DNASE I

This Application is a continuation-in-part and claims priority based on U.S. patent application Ser. No. 10/404,023, filed Mar. 31, 2003 now abandoned. Without limiting the scope of the invention, its background is described in connection with polydeoxyribonucleic acid hydrolases, as an example.

TECHNICAL FIELD OF THE INVENTION

The present invention relates in general to the field of polydeoxyribonucleic acid hydrolases, and more particularly, to compositions and methods of using a synthetic bovine DNase I.

BACKGROUND OF THE INVENTION

Deoxyribonuclease (DNase) is a phosphodiesterase capable of hydrolyzing polydeoxyribonucleic acid into individual 3' or 5'-phosphate deoxynucleotides on hydrolysis of deoxyribonucleic acid (DNA). Based on their biochemical properties and enzymatic activities, DNase proteins have been classified as two types, DNase I and DNase II. DNase I proteins have a pH optimum near neutral and an obligatory requirement for divalent cations, and create 5'-phosphate deoxynucleotide products. DNase II has an acid pH optimum, can be activated by divalent cations, and produces 3'-phosphate deoxynucleotides on hydrolysis of DNA.

The nucleic acid encoding a human DNase I has been isolated, sequenced and the protein expressed in recombinant host cells, thereby enabling the production of human DNase I in commercially useful quantities. The DNA encoding other polypeptides having homology to human DNase I have also been identified.

Human DNase I has recently been used to reduce the viscoelasticity of pulmonary secretions (mucus) in such diseases as pneumonia and cystic fibrosis (CF), thereby aiding in the clearing of respiratory airways. One such pharmaceutical composition is described by U.S. Pat. No. 6,440,412, issued to Frenz, et al., for purified forms of DNase I in which the DNase is provided in a formulation for use in administering to patients suffering from pulmonary distress.

One such formulation is sold under the tradename Pulmozyme® (dornase alfa, Genentech, USA), in which the recombinant human deoxyribonuclease I (rhDNase) is provided to a patient in an inhaled solution that is sterile, clear, colorless, and contains a highly purified solution of rhDNase. The characteristics of the rhDNase were selected to attack pulmonary secretions of persons having such diseases are complex materials, which include mucus glycoproteins, mucopolysaccharides, proteases, actin and DNA. rhDNase I was found to be effective in reducing the viscoelasticity of pulmonary secretions by hydrolyzing, of degrading, high-molecular-weight DNA that is present in such secretions.

A hyperactive rhDNase is described by U.S. Pat. No. 6,391,607, issued to Lazarus, et al., for human DNase I hyperactive variants, in which amino acid sequence variants of human DNase I that have increased DNA-hydrolytic activity are disclosed. The patent disclosure describes nucleic acid sequences encoding such hyperactive variants, thereby enabling the production of these variants in quantities sufficient for clinical use. The invention also relates to pharmaceutical compositions and therapeutic uses of hyperactive variants of human DNase I.

SUMMARY OF THE INVENTION

The present invention is based on the recognition that DNase I molecules of the prior art fail to have features that permit their expression at high levels and with biochemical characteristics that enhance their usefulness. The present inventors have developed a modified DNase I molecule that possesses heretofore unknown characteristics. These new and unexpected characteristics or properties are particularly useful as compared to the unmodified or wild-type enzyme and offers significant improvements to several very common molecular biology manipulations. While similar mutants have been made in human DNase I for use as a therapeutic agent, the modified or synthetic bovine DNase I mutant of the present invention was designed to overcome a number of problems in the art, namely, ease of expression and purification and scalability. Subsequent evaluation revealed that not only was the expression and availability enhanced, new features were discovered that permit the use of the DNase I of the present invention in a number of assays in which it was heretofore contraindicated.

One problem with wild-type DNase I is its modest $K_m$ (~600 nM) for model dsDNA substrates, which makes it unsuitable at low concentrations of enzyme and substrate. Furthermore, wild-type DNase I is inhibited in solutions containing modest salt concentrations, and the ionic strength of typical molecular biology buffers profoundly inhibit enzyme activity. The modification of the DNase I of the present invention provides an improvement to one or more of these properties to provide an enzyme with greater effectiveness and range of use for molecular biology applications.

As a result of this need, the present inventors sought to develop a functionally superior DNase I. Amino acids in the DNA binding cleft of human DNase I (hDNase I) could be mutated to basic residues to promote tighter binding by the enzyme. The major effect of this change is to lower the $K_m$ of the enzyme for dsDNA. Depending on the nature of the assay, some mutant human DNase I enzymes also exhibited higher $V_{max}$ values. Some human mutant enzymes are also highly resistant to relatively high concentrations of NaCl. For therapeutic uses these mutants have been shown to be active in physiological saline.

The present invention includes a synthetic bovine DNase I (sbDNase I) mutant that was designed, developed and discovered to exhibit several desirable properties as compared to wild-type DNase I. For example, variants of sbDNase I described herein have an up to 20-fold lower $K_m$ than wild-type DNase I. The enzyme of the present invention is also salt-tolerant, that is, it maintains at least 30% of peak activity from 0–200 mM NaCl, whereas the wild-type enzyme does so only from 0–40 mM. Thus, sbDNase I is a versatile enzyme that can be added directly to most molecular biology buffers without a significant loss in activity. Importantly, the salt tolerance of sbDNase I can be "ratcheted" up or down by altering the $Ca^{2+}$ concentration; thereby providing a molecular switch that can be used to turn the enzyme on and off by either adding a divalent cation (like calcium) or removing the cations using, e.g., EDTA, EGTA or other chelating agent. Furthermore, when manufactured in a non-mammalian expression system, sbDNase I is ~$10^7$-fold less contaminated with RNase activity than bovine pancreas. For example, it has been found that $\geq 20$ U sbDNase I failed to degrade significantly a radiolabeled RNA transcript, whereas, the wild-type enzyme causes obvious degradation of said probe at above 10 U. When expressed in a non-mammalian expression system the ease of production is improved, costs are reduced and the need for mammalian tissue culture systems eliminated.

The sbDNase I of the present invention is a versatile enzyme that cleaves DNA nonspecifically to release 5'-phosphorylated di-, tri-, and oligonucleotide products. The sbDNase I may be used for a wide range of molecular biology applications, including: degradation of contaminating DNA after RNA isolation; "clean-up" of RNA prior to RT-PCR and after in vitro transcription; removal of DNA prior to protein sample loading on 2-D gels; identification of protein binding sequences on DNA (DNase I footprinting); prevention of clumping when handling cultured cells; and creation of a fragmented library of DNA sequences for in vitro recombination reactions.

More particularly, the present invention includes an isolated, synthetic nucleic acid molecule that has an optimized nucleotide sequence having at least about an 85 to 95%, 90 to 95%, 95 to 100% or even about 100% identity with an nucleic acid sequence of SEQ ID NO.: 1, SEQ ID NO.: 3 or SEQ ID NO.: 19 for a recombinant bovine DNase I, that encodes an amino acid sequence of SEQ ID NO.: 2, SEQ ID NO.: 4 or SEQ ID NO.: 20 for a bovine DNase I. For example, the synthetic DNase I may be a synthetic bovine DNase I that is optimized for microbial expression, e.g., in a bacteria, yeast, plant or other eukaryotic cell. The optimized sequence may also include an E13R mutation, an N74K mutation or both an E13R mutation and an N74K mutation, a leader sequence, a secretory leader sequence, a fusion protein partner, a pelB leader sequence, a yeast alpha mating factor protein and the like.

The present invention also includes an expression vector that includes a nucleotide sequence encoding the amino acid sequence for a synthetic bovine DNase I operably linked to a promoter recognized by a host cell transformed with the vector. The host cell may be a yeast cell, e.g., *Pichia pastoris*. In one embodiment the nucleic acid molecule includes a nucleotide sequence that encodes an nucleic acid sequence having at least about an 85 to 95%, 90 to 95%, 95 to 100% or even about 100% identity with an nucleic acid sequence of SEQ ID NO.: 1, SEQ ID NO.: 3 or SEQ ID NO.: 19 for a recombinant bovine DNase I as determined by sequence comparison or even using high stringency hybridization.

The present invention also includes a process for making a bovine DNase I that includes the steps of; transforming a host cell with a nucleic acid molecule of SEQ ID NO.: 1, SEQ ID NO.: 3 or SEQ ID NO.: 19 that encodes the bovine DNase I including an amino acid sequence of SEQ ID NO.: 2, SEQ ID NO.: 4 or SEQ ID NO.: 20, respectively, and culturing the host cell under conditions such that the bovine DNase I is produced in the host cell. The host cell may be a eukaryotic cell, e.g., a *Pichia pastoris* host cell, which may produce the DNase I protein of the present invention to a level of at least 1 mg/L bovine DNase I protein. The synthetic bovine DNase I may even be made by the process described hereinabove.

Another embodiment of the present invention is a synthetic bovine DNase I enzyme prepared by a process that includes the steps of; expressing a synthetic bovine DNase I in a eukaryotic host cell transformed with an expression vector that includes a DNA sequence of SEQ ID NO.: 1, SEQ ID NO.: 3 or SEQ ID NO.: 19, encoding an amino acid sequence of SEQ ID NO.: 2, SEQ ID NO.: 4 or SEQ ID NO.: 20 for a synthetic bovine DNase I and purifying the synthetic bovine DNase I from the cultured eukaryotic host cell.

The present invention may be used for a number of life science applications that were heretofore not possible due to the limitations of wild-type, purified DNase I proteins available in the art. For example, the present invention may be used in a method of in vitro DNA removal that includes the steps of: mixing a solution suspected of having DNA with a synthetic DNase I having a Km of less than 600 nM in a DNase I buffer. The present invention also includes a method for degrading contaminating DNA during or after RNA isolation (e.g., when the DNase is used for on-column DNA removal before elution of RNA from a solid support), hydrolyzing DNA after in vitro transcription, hydrolyzing DNA after in vitro transcription and prior to PCR, identifying protein binding sequences on DNA, for DNase I footprinting, to prevent clumping of cultured cells in vitro, for tissue dissociation, for creating a fragmented library of DNA sequences for in vitro recombination reactions and even to remove DNA from common solutions or even to remove DNA from a 2-D gel sample.

The sbDNase I of the present invention has significant activity in DNase I buffers with an ionic strength greater than 25 mM. The sbDNase I has over 50% of wild-type activity in such a buffer, e.g., a medium to high ionic strength, in a low concentration of calcium and/or in an RT-PCR buffer or combinations thereof. The recombinant DNase I of the present invention may be used for RNA isolation, e.g., before, during and/or after RNA isolation.

The present invention also includes a DNase I and a method for purifying a synthetic DNase I that includes the steps of: loading a concentrated, dialyzed cell supernatant that includes a synthetic DNase I onto an SP column, eluting and collecting fractions of the synthetic DNase I with a 0–1 M NaCl gradient, dialyzing one or more fractions that contain DNase I activity, loading the dialyzed one or more fractions onto a Q and eluting and collecting fractions of the synthetic DNase I with a 0–0.1 M $CaCl_2$ gradient.

The present invention is also a kit for removing DNA from a solution, which includes in a suitable container, a synthetic DNase I and a reaction solution with an ionic strength greater than 25 mM. The kit may also include information for using the synthetic DNase I, e.g., a leaflet, link to a website, a CD, a DVD or other instructional material. In one embodiment the reaction solution may be a concentrated solution, e.g., a 10× concentrated reaction solution, which may even include a buffer. The kit may also include a divalent cation chelator, a DNase removal agent, an RT buffer, a PCR buffer, a single-step RT-PCR buffer and the like.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which:

FIG. 1 shows the nucleotide coding sequence of the synthetic bovine DNase I gene of the present invention (SEQ ID NO.: 1);

FIG. 2 shows another nucleotide coding sequence for a synthetic bovine DNase I gene of the present invention (SEQ ID NO.: 3);

FIG. 3A is the sequence of the pPicZαA_sbDNase I 4315 bp that includes the Xho I and Not I restriction sites that were used to insert the sbDNase I gene are shown underlined (SEQ ID NO.: 19);

FIG. 3B is the amino acid sequence for a recombinant DNase I, optimized for expression and including the alpha mating factor leader sequence and mature protein (SEQ ID NO.: 20);

FIG. 4 is an alignment of the naturally-occurring bovine DNase I coding sequence (SEQ ID NO.: 21) with a codon-optimized synthetic bovine DNase I gene sequence of the present invention (SEQ ID NO.: 1);

DETAILED DESCRIPTION OF THE INVENTION

Figure 5:
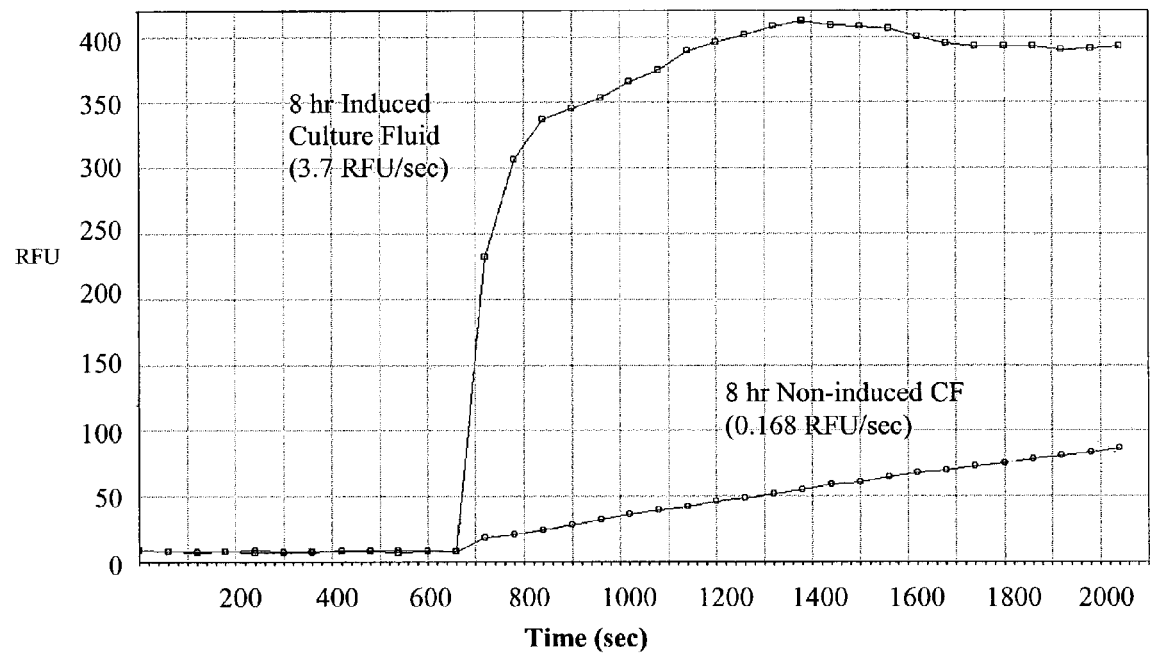
FIG. 5 is a graph that shows a >20-fold increase in DNA cleaving activity when *E. coli* culture fluid is compared before and after sbDNase I induction.

While the making and using of various embodiments of the present invention are discussed in detail below, it should be appreciated that the present invention provides many applicable inventive concepts that may be embodied in a wide variety of specific contexts. The specific embodiments discussed herein are merely illustrative of specific ways to make and use the invention and do not delimit the scope of the invention.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

As used throughout the present specification the following abbreviations are used: TF, transcription factor; ORF, open reading frame; kb, kilobase (pairs); UTR, untranslated region; kD, kilodalton; PCR, polymerase chain reaction; RT, reverse transcriptase.

As defined herein, a "wild type" sequence, whether found in a coding, non-coding or interface sequence is an allelic form of sequence that performs the natural or normal function for that sequence. As used throughout the specification, the wild-type DNase I used as a source of a comparable enzyme is purified bovine pancreatic DNase I.

By the term "sbDNase I" or "synthetic bovine DNase I" or grammatical equivalents herein is meant a polypeptide having a modified amino acid sequence of bovine mature DNase I as described herein, as well as amino acid sequence variants that are enzymatically active in hydrolyzing DNA with a catalytic profile that is distinct from that of wild type DNase I. In specific embodiments, specific amino acid point mutants are also described using well-established nomenclature, as will be known to the skilled artisan. An enzymatic profile that is distinct from wild type bovine DNase I may be determined as described herein and may include, e.g., a determination of Km, Vmax, sensitivity to ionic, salts or salt concentration(s), ionic strength, availability of cations, temperature and combinations thereof. Thus, the terms herein denote a broad definition of those materials disclosed and prepared in the various examples provided herein. It will be understood that the terms include both purified mixtures of deamidated and non-deamidated bovine DNase as well as purified forms of each.

A "synthetic" or "recombinant" nucleic acid and its underlying sequence is defined herein as being any nucleic acid, native or otherwise, that is transferred by molecular biology methods, e.g., isolating a nucleic acid having a particular sequence, and transferring the nucleic acid to an alternative host for manipulation. An "optimized" sequence is one in which at least a portion of the sequence has been modified by directed sequence modification, for example, changes to the sequence in one or more underlying sequences that may or may not affect the amino acid sequence but that are use to, e.g., improve the expression of the protein by using codons that are more commonly used in a particular host organism. By the term "recombinant," "isolated," "cloned" DNase I or grammatical equivalents herein is meant a polypeptide having a modified nucleic or amino acid sequence of a mature DNase I (for example, from about 85 to 100% identical) as described herein, as well as amino acid sequence variants that are enzymatically active in hydrolyzing DNA with a catalytic profile that is distinct from that of wild type DNase I. In addition, sequences may be the combination of sequences from different organisms for the same or closely related sequences to, e.g., modify the functionality of the final protein by directed modifications or even to permit specific recombinant modification or manipulation by the user. The G-D-F-N-A-x-C-S/A sequence is a DNase I motif that distinguishes this family of enzymes from others as described by, e.g., PROSITE. The DNase I of the present invention may be expressed in *Pichia pastoris*, and may include rat, rabbit, and other DNase I proteins using the present invention.

The synthetic region or regions of modification will generally affect, e.g., the expression of an amino acid from the coding sequence in a host organism. A "mutation" in a synthetic sequence as used herein is any change in a nucleic acid sequence that may arise such as from a deletion, addition, substitution or rearrangement of the nucleic acid sequences. For example, a change in a DNA sequence may lead to the synthesis of an altered protein, one that has a modified activity profile as compared to the wild-type sequence or to permit a host cell to be able to produce the protein.

The terms "a sequence essentially as set forth in SEQ ID NO. (#)", "a sequence similar to", "a nucleic acid sequence" and similar terms, with respect to nucleotide sequences, refers to sequences that correspond substantially to any portion of the sequence identified herein under a SEQ ID NO. A like designation is used herein for amino acid sequences. These terms refer to synthetic molecules and include sequences that possess biologically, immunologically, experimentally, or otherwise functionally equivalent activity, for instance with respect to hybridization by nucleic acid segments to, e.g., SEQ ID NOS.: 1, 3 and 19, or the ability to encode all or portions of the synthetic bovine DNase I, e.g., the amino acids of SEQ ID NOS.: 2, 4 and 20, or functional equivalents thereof. Naturally, these terms are meant to include information in such a sequence as specified by its linear order.

The term "homology" refers to the extent to which two nucleic acids are complementary. There may be partial or complete homology. A partially complementary sequence is one that at least partially inhibits a completely complementary sequence from hybridizing to a target nucleic acid and is referred to using the functional term "substantially homologous." The degree or extent of hybridization may be examined using a hybridization or other assay (such as a competitive PCR assay) and is meant, as will be known to those of skill in the art, to include specific interaction even at low stringency.

A "sample" is one or more solutions or powders that may is, or may be dissolved in, an aqueous medium. A sample as described herein is used for in vitro assays, e.g., life science applications. Sample includes, but is not limited to, supernatants, isolated (fully or partially) nucleic acids, proteins, tissue supernatants, cell supernatants, cell extracts, and the like. Other sources of samples may include: blood, plasma, urine, semen, saliva, lymph fluid, meningeal fluid, amniotic fluid, glandular fluid, and cerebrospinal fluid. Samples also include fractions separated, solutions or mixtures containing known or unknown components and may be obtained at any point in time, including diagnosis, prognosis, and periodic monitoring. Specific examples of samples as described herein below for samples used in life sciences applications, e.g., removal of DNA from laboratory solutions, reverse transcription and the like.

As used herein, the term "vector" is used in reference to nucleic acid molecules used to transfer DNA segment(s) from one cell to another. A "vector" may also include expression vectors in reference to a recombinant DNA molecule containing a desired coding sequence and appropriate nucleic acid sequences necessary for the expression of the operably linked coding sequence in a particular host organism. Nucleic acid sequences necessary for expression in prokaryotes usually include: a promoter, an operator (optional), and a ribosome binding site and/or other sequences. Eukaryotic cell vectors will usually include: promoters, enhancers and/or other sequences, e.g., termination and polyadenylation signals. The vector may exist in a state independent of the host cell chromosome, or may be integrated into the host cell chromosome.

The term "host cell" refers to cells that have been engineered to contain nucleic acid segments or altered segments, whether archael, prokaryotic or eukaryotic. Thus, engineered, or recombinant cells, are distinguishable from naturally occurring cells that do not contain genes introduced by recombinant methods through the hand of man.

The term "altered", or "alterations" or "modified" with reference to nucleic acid or polypeptide sequences is meant to include changes such as insertions, deletions, substitutions, fusions with related or unrelated sequences, such as might occur by the hand of man. Examples of each of these modifications are shown in the examples herein. Alterations encompass genomic DNA and RNA sequences that may differ with respect to their hybridization properties using a given hybridization probe. Alterations to the polynucleotide sequences of bovine DNase I, or fragments thereof, include those that increase, decrease, or have no effect on expression, stability and/or functionality as disclosed herein. Alterations of polypeptides refer to those that have been changed by recombinant DNA engineering, although additional modifications such as chemical, or biochemical modifications, such as amino acid derivatives or conjugates, or post-translational modifications are also included.

A nucleic acid is "operably linked" when it is placed into a functional relationship with another nucleic acid sequence.

For example, DNA for a presequence or secretory leader is operably linked to DNA for a polypeptide if it is expressed as a fusion protein that participates in the secretion of the polypeptide; a promoter or enhancer is operably linked to a coding sequence if it effects the transcription of the sequence; or a ribosome binding site is operably linked to the coding sequence if it is positioned so as to facilitate translation. Generally, "operably linked" means that the DNA sequences being linked are contiguous and, in the case of a secretory leader, contiguous and in same reading frame.

As used herein, the expressions "cell" and "cell culture" are used interchangeably and all such designations include progeny. Thus, the words "transformants" and "transformed cells" include the primary subject cell and cultures derived therefrom without regard for the number of generations or transfers. It is also understood that all progeny may not be precisely identical in DNA content, due to deliberate or inadvertent mutations. Mutant progeny that have the same function or biological activity as screened for in the originally transformed cell are included.

As used herein, the term "catalytic" or "catalytic activity" refers to the ability of the sbDNase I of the present invention to hydrolyze a polydeoxyribonucleic acid substrate under permissive conditions. As used herein, the term "kinetic parameters" refers to, e.g., catalytic activity, in this case hydrolysis of a double-stranded DNA substrate. Changes in the kinetic parameters of a nuclease include changes to the catalytic activity of the nuclease such as a change in the rate of reaction or a change in substrate specificity. Changes may also include the allosteric effects of, e.g., salt concentration, presence or absence of cations and anions, pH, temperature, specificity and the like.

More particularly, "DNA-hydrolytic activity," "DNAse activity" or grammatically equivalents thereof, refers to the enzymatic activity of a DNase I, a synthetic bovine DNase I or a variant of the synthetic DNase I that hydrolyzes a DNA substrate to yield 5'-phosphorylated oligonucleotide end products. DNA-hydrolytic activity is readily determined by any of several different methods known in the art, including analytical polyacrylamide and agarose gel electrophoresis, fluorescence resonance energy transfer (FRET) assay (DNaseAlert™ assay), hyperchromicity assay and other assays as disclosed herein. An sbDNase I variant having "modified DNA-hydrolytic activity" is one that hydrolyzes DNA to a greater or lesser extent than native DNase I, e.g., human or bovine DNase I as determined under comparable conditions.

The term "ionic strength" refers to the relationship between ion charge and concentration to provide the sum total of charge equivalents in solution. Ionic strength is defined according to: $\mu = 1/2 \Sigma c_i Z_i^2$, where $\mu$ is the ionic strength, $c_i$ is the concentration of the ith ion, and $Z_i$ is the net charge on the ith ion. In a broad sense, the ionic strength of the solution reflects the concentration of cations and anions. Generally, a buffer having a medium ionic strength will be between about 50 to 250 mM and a buffer with a high ionic strength is at between about 250 to 500 mM. When referring to calcium, a buffer having a low concentration of calcium will have between about 0.05 to 1 mM.

For example, if the DNaseAlert™ FRET assay described in the examples is used to determine DNA-hydrolytic activity, then a synthetic bovine DNase I variant having increased DNA-hydrolytic activity will be one having an activity greater than native bovine DNase I in the assay as determined under comparable conditions. In some cases the assay may require that the activity of the synthetic variant be decreased or eliminated as compared to the wild-type DNase I. In any such assay, a synthetic bovine DNase I will typically have at least 50% greater DNA-hydrolytic activity than native bovine DNase in solutions having an ionic strength of greater than 25 mM, however, some variants having upwards of 10-fold greater DNA-hydrolytic activity than native bovine DNase I also are readily produced, especially by altering multiple amino acid residues of the native bovine DNase I amino acid sequence (see e.g., FIGS. 1A, 1B, 2A and 2B and the examples herein).

The term "gene" is used to refer to a functional protein, polypeptide or peptide-encoding unit. As will be understood by those in the art, this functional term includes both genomic sequences, cDNA sequences, or fragments or combinations thereof, as well as gene products, including those that may have been altered by the hand of man. Purified or isolated genes, nucleic acids, protein and the like are used to refer to these entities when identified and separated from at least one contaminating nucleic acid or protein with which it is ordinarily associated. The term "sequences" as used herein is used to refer to nucleotides or amino acids. When describing "transcribed nucleic acids" those sequence regions located adjacent to the coding region on both the 5', and 3', ends such that the deoxyribonucleotide sequence corresponds to the length of the full-length mRNA for the protein are included. As used herein the terms "protein", "polypeptide" or "peptide" refer to compounds in which amino acids joined via peptide bonds and are used interchangeably.

The term "hybridize" as used herein, refers to any process by which a strand of nucleic acid binds with a complementary strand through base pairing. Hybridization and the strength of hybridization (i.e., the strength of the association between the nucleic acid strands) is impacted by such factors as the degree of complementary between the nucleic acids, stringency of the conditions involved, the melting temperature of the formed hybrid, and the G:C (or U:C for RNA) ratio within the nucleic acids. In addition to sequence information, it is possible to determine if a nucleic acid has 85, 90, 95 or even 100% indentity by hybridization at high stringency. High stringency conditions include conditions equivalent to binding or hybridization at 65° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5× Denhardt's reagent (50× Denhardt's contains per 500 ml: 5 g Ficoll (Type 400, Pharmacia), 5 g BSA [Fraction V; Sigma]) and 100 µg/ml denatured salmon sperm DNA) followed by washing in a solution comprising 5×SSPE, 01% SDS at 65° C. when a probe of about 500 nucleotides in length is employed. Numerous equivalent conditions may be employed to vary stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low or high stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

The terms "complementary" or "complementarity" as used herein, refer to the natural binding of polynucleotides under permissive salt and temperature conditions by base-pairing. For example, for the sequence "A-G-T" binds to the complementary sequence "T-C-A." The degree of complementarity is of particular importance in amplification reactions, which depend upon binding between nucleic acids strands.

Percent similarity and percent identity may be determined, for example, by comparing sequence information using, e.g., CLUSTAL or GAP, computer programs available from the University of Wisconsin Genetics Computer Group (UWGCG). Such programs define similarity as the number of aligned symbols (i.e., nucleotides or amino acids) that are similar, divided by the total number of symbols in the shorter of the two sequences. The term "identity," as used herein, refers to the percentage of or nucleic or amino acids that are identical at a like position in a sequence alignment, i.e., complete homology.

"Transformation," as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection and particle bombardment. Such transformed cells include cells transformed stably in which the inserted DNA is capable of replication either as an autonomously replicating plasmid or as part of the host chromosome.

The term "transfection" as used herein refers to the introduction of foreign DNA into eukaryotic cells. Transfection may be accomplished by a variety of methods, e.g., calcium phosphate-DNA co-precipitation, DEAE-dextran-mediated transfection, polybrene-mediated transfection, electroporation, microinjection, liposome fusion, lipofection, protoplast fusion, retroviral infection, and biolistics. Thus, the term "stable transfection" or "stably transfected" refers to the introduction and integration of foreign DNA into the genome of the transfected cell. The term "stable transfectant" refers to a cell which has stably integrated foreign DNA into the genomic DNA. The term also encompasses cells that express transiently the inserted DNA or RNA for limited periods of time. Thus, the term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells which have taken up foreign DNA but have failed to integrate this DNA.

As used herein, the term "selectable marker" refers to the use of a gene that encodes an enzymatic activity and which confers the ability to grow in medium lacking what would otherwise be an essential nutrient (e.g., the HIS3 gene in yeast cells); in addition, a selectable marker may confer resistance to an antibiotic or drug upon the cell in which the selectable marker is expressed. A review of the use of selectable markers in mammalian cell lines is provided in Sambrook, J., et al., MOLECULAR CLONING: A LABORATORY MANUAL, 2nd ed., Cold Spring Harbor Laboratory Press, New York (1989) pp.16.9–16.15.

As used herein, the term "amplify", when used in reference to nucleic acids refers to the production of a large number of copies of a nucleic acid sequence by any method known in the art. Amplification is a special case of nucleic acid replication involving template specificity. Template specificity is frequently described in terms of "target" specificity. Target sequences are "targets" in the sense that they are sought to be sorted out from other nucleic acid. Amplification techniques have been designed primarily for this sorting out.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer may be single stranded for maximum efficiency in amplification but may alternatively be double stranded. If double stranded, the primer is first treated to separate its strands before being used to prepare extension products. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is not intended that the present invention be limited to any particular detection system or label.

As used herein, the term "target" when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis, e.g., U.S. Pat. Nos. 4,683,195, 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular the amplified segments created by the PCR process itself are, themselves, efficient templates for subsequent PCR amplifications.

The term "reverse transcription" refers to a reaction in which an RNA template is reverse transcribed using any of the known reverse transcriptase enzymes into a complementary DNA (cDNA) chain. A reverse transcription reaction will include, generally: enzymes, aqueous buffers, salts, oligonucleotide primers, target nucleic acid and nucleoside triphosphates. Depending upon the context, the mixture can be either a complete or incomplete reverse transcription reaction mixture.

For amplification of the cDNA product a number of methods are available to one of ordinary skill in the art. As used herein the term "amplification" refers to any in vitro means for multiplying the copies of a target sequence of nucleic acid. Such methods include but are not limited to polymerase (PCR), DNA ligases, RNA replicase, and RNA transcription-based (TAS and 3SR) amplification systems and the like.

The term "amplification" refers to an aqueous solution that includes the various reagents used to amplify a target nucleic acid. An amplification reaction will include, generally: enzymes, aqueous buffers, salts, amplification primers, target nucleic acid and nucleoside triphosphates. Depending upon the context, the mixture can be either a complete or incomplete amplification reaction mixture. Generally, the amplification system is a PCR amplification system.

EXAMPLE 1

Expression of a Synthetic Bovine DNase I in *E. coli*. DNase I is an extremely toxic protein in *E. coli*. Inasmuch as this enzyme readily degrades dsDNA, active DNase I in the cytoplasm will cleave bacterial chromosomal DNA and kill the cell. In fact, an effective concentration of DNase I for clearing DNA contamination in advance of RT-PCR (~2.5 nM) is approximately the same as that of a single DNase I molecule in an *E. coli* cell (assuming a cell volume of ~1 fL). As a result, non-conventional strategies must be considered to successfully express this protein in reasonably high yield (>5 mg/L).

The coding portion of the gene for the synthetic bovine DNase I (sbDNase I) was created by assembling oligodeoxynucleotides that were synthesized de novo (FIG. 1). For common molecular biology and protein expression manipulations, procedures were performed as described in *Molecular Cloning: A Laboratory Manual* (Cold Spring Harbor Press) or *Current Protocols in Molecular Biology* (J. Wiley and Sons). The steps for creation of the sbDNase I genes of the present invention were as follows: 1) Design. When appropriate, silent mutations in the gene that eliminated rare codons in *E. coli* were introduced in an attempt to optimize expression in *E. coli* (FIGS. 1, 2, 3A and 4). For example, the third codon of the gene the naturally-occurring "ATA" codon that codes for Ile was changed to "ATC" (Ile) since the latter is roughly 6-fold more common in host genes.

Altogether, seventy-eight such silent mutations were created. 2) DNA synthesis. Oligodeoxynucleotides corresponding to 80–100 base regions in the sequence were synthesized and purified by polyacrylamide gel electrophoresis. 3) Assembly. Complementary oligonucleotides were annealed, ligated, and cloned into a commercial plasmid vector, pZErO-2. 4) Sequence verification. Clones were sequenced to confirm the authenticity of the gene in the final construct. 5) Purification. Plasmid DNA was amplified in an *E. coli* host, and purified by standard methods.

TABLE 1

Sequence Alignment of Mammalian DNase I Proteins

CLUSTAL W (1.8) multiple sequence alignment

```
Bovine_DNase_precursor      MRGTRLMGLLLALAGLLQLGLSLKIAAFNIRTFGETKMSNATLASYIVRI
Synthetic_Bovine_DNase_I    ----------------------MKIAAFNIRTFGETKMSNATLASYIVRI
Sheep_DNase_I               ----------------------LKIAAFNIRTFGETKMSNATLSSYIVRI
Pig_DNase_I                 ----------------------LRIAAFNIRTFGETKMSNATLSNYIVRI
Rat_DNase_I                 MRYTGLMGILLTLVNLLQLAATLRIAAFNIRTFGDTKMSNATLSSYIVKI
Mouse_DNase_I               MRYTGLMGTLLTLVNLLQLAGTLRIAAFNIRTFGETKMSNATLSVYFVKI
Human_DNase_I_precursor     MRGMKLLGALLALAALLQGAVSLKIAAFNIQTFGETKMSNATLVSYIVQI
Rabbit_DNase_I              MR-SEMLTALLTLAVLLQVAGSLKIAAFNIRSFGETKMSNATLTSYIVRI
LS-DNase                    --MSRELAPLLLLLLSIHSALAMRICSFNVRSFGESKQEDKNAMDVIVKV
                              ::*..:**::**::* .: .    :*::

Bovine_DNase_I_precursor    VRRYDIVLIQEVRDSHLVAVGKLLDYLNQDDPN--TYHYVVSEPLGRNSY
Synthetic_Bovine_DNase_I    VRRYDIVLIQEVRDSHLVAVGKLLDYLNQDDPN--TYHYVVSEPLGRNSY
Sheep_DNase_I               LRRYDIALIEQVRDSHLVAVGKLLDDLNQDDPN--SYHYVVSEPLGRNSY
Pig_DNase_I                 LSRYDIALIQEVRDSHLTAVGKLLNELNQDDPN--NYHHVVSEPLGRSTY
Rat_DNase_I                 LSRYDIAVVQEVRDTHLVAVGKLLDELNRDIPD--NYRYIISEPLGRKSY
Mouse_DNase_I               LSRYDIAVIQEVRDSHLVAVGKLLDELNRDKPD--TYRYVVSEPLGRKSY
Human_DNase_I_precursor     LSRYDIALVQEVRDSHLTAVGKLLDNLNQDAPD--TYHYVVSEPLGRNSY
Rabbit_DNase_I              LQRYDIALIQEVRDSHLTAVGKLLDKLNEKAAD--TYRFVASEPLGRRTY
LS-DNase                    IKRCDIILVMEIKDSNNRICPILMEKLNRNSRRGITYNYVISSRLGRNTY
                            : * ** :: :::*::     *::  **..    .*..: *. *** :*

Bovine_DNase_I_precursor    KERYLFLFRPNKVSVLDTYQYDDGCESCGNDSFSREPAVVKFSSHSTKVK
Synthetic_Bovine_DNase_I    KERYLFLFRPNKVSVLDTYQYDDGCESCGNDSFSREPAVVKFSSHSTKVK
Sheep_DNase_I               KERYLFVFRPNKVSVLDTYQYDDGCESCGNDSFSREPAVVKFSSPSTKVK
Pig_DNase_I                 KERYLFVFRPNQVSVLDSYLYDDGCEPCGNDTFNREPSVVKFSSPFTQVK
Rat_DNase_I                 KEQYLFVYRPSQVSVLDSYHYDDGCEPCGNDTFSREPAIVKFFSPYTEVR
Mouse_DNase_I               KEQYLFVYRPDQVSILDSYQYDDGCEPCGNDTFSREPAIVKFFSPYTEVQ
Human_DNase_I_precursor     KERYLFVYRPDQVSAVDSYYYDDGCEPCGNDTFNREPAIVRFFSRFTEVR
Rabbit_DNase_I              KERYLFVYRPDQVSVLDSYYYDDGCEPCGTDTFSREPAVVRFSSPSTKVR
LS-DNase                    KEQYAFLYKEKLVSVKRSYHYHD-YQDGDADVFSREPFVVWFQSPHTAVK
                            **:* *::: . **   :* *.*  :  . * *.*** :* * *  * *:

Bovine_DNase_I_precursor    EFAIVALHSAPSDAVAEINSLYDVYLDVQQKWHLNDVMLMGDFNADCSYV
Synthetic_Bovine_DNase_I    EFAIVALHSAPSDAVAEINSLYDVYLDVQQKWHLNDVMLMGDFNADCSYV
Sheep_DNase_I               AFAIVPLHSAPSDAVAEINSLYDVYLDVQQKWDLNDIMLMGDFNADCSYV
Pig_DNase_I                 EFAIVPLHAAPSDAAAEINSLYDVYLNVRQKWDLQDIMLMGDFNAGCSYV
Rat_DNase_I                 EFAIVPLHSAPTEAVSEIDALYDVYLDVRQKWGLEDIMFMGDFNAGCSYV
Mouse_DNase_I               EFAIVPLHAAPTEAVSEIDALYDVYLDVWQKWGLEDIMFMGDFNAGCSYV
Human_DNase_I_precursor     EFAIVPLHAAPGDAVAEIDALYDVYLDVQEKWGLEDVMLMGDFNAGCSYV
Rabbit_DNase_I              EFAIVPLHSAPEDAVAEIDALYDVYLDVQKKWGLQDVMLMGDFNADYSYV
LS-DNase                    DFVIIPLHTTPETSVKEIDELVEVYTDVKHRWKAENFIFMGDFNAGCSYV
                            *.*:.**:* :. **: * :** :* ..:*  ::.:;******. ***

Bovine_DNase_I_precursor    TSSQWSSIRLRTSSTFQWLIPDSADTTAT-STNCAYDRIVVAGSLLQSSV
Synthetic_Bovine_DNase_I    TSSQWSSIRLRTSSTFQWLIPDSADTTAT-STNCAYDRIVVAGSLLQSSV
Sheep_DNase_I               TSSQWSSIRLRTSSTFQWLIPDSADTTAT-STNCAYDRIVVAGSLLQSSV
Pig_DNase_I                 TTSHWSSIRLRESPPFQWLIPDTADTTVS-SHTCAYDRIVVAGPLLQRAV
Rat_DNase_I                 TSSQWSSIRLRTSPIFQWLIPDSADTTAT-STHCAYDRIVVAGALLQAAV
Mouse_DNase_I               TSSQWSSIRLRTSPIFQWLIPDSADTTVT-STHCAYDRIVVAGALLQAAV
Human_DNase_I_precursor     RPSQWSSIRLWTSPTFQWLIPDSADTTAT-PTHCAYDRIVVAGMLLRGAV
Rabbit_DNase_I              TSSQWSSIRLRTNPAFKWLIPDTADTTAT-STNCAYDRIVVAGPLLQDAV
LS-DNase                    PKKAWKNIRLRTDPRFVWLIGDQEDTTVKKSTNCAYDRIVLRGQEIVSSV
                            . *..***  .. * *** *  ***.. .  *******: * :  :*

Bovine_DNase_I_precursor    VPGSAAPFDFQAAYGLSNEMALAISDHYPVEVTLT---------------
Synthetic_Bovine_DNase_I    VPGSAAPFDFQAAYGLSNEMALAISDHYPVEVTLT---------------
Sheep_DNase_I               VGPSAVPFDFQAAYGLSNEMALAISDHYPVEVTLT---------------
Pig_DNase_I                 VPDSAAPFDFQAAFGLSQETALAISDHYPVEVTLKRA-------------
Rat_DNase_I                 VPSSAVPFDFQAEYRLTNQMAEAISDHYPVEVTLRKT-------------
Mouse_DNase_I               VPNSAVPFDFQAEYGLSNQLAEAISDHYPVEVTLRKI-------------
Human_DNase_I_precursor     VPDSALPFNFQAAYGLSDQLAQAISDHYPVEVMLK---------------
Rabbit_DNase_I              VPNSAAPFNFQAAYGLSNQLAQAISDHYPVEVTLA---------------
LS-DNase                    VPKSNSVFDFQKAYKLTEEEALDVSDHFPVEFKLQSSRAFTNSKKSVTLR
                            *  *   *:**  : *:::  *  :***;***. *

Bovine_DNase_I_precursor    --------  SEQ ID NO.:5
Synthetic_Bovine_DNase_I    --------  SEQ ID NO.:2
```

TABLE 1-continued

Sequence Alignment of Mammalian DNase I Proteins

| | | |
|---|---|---|
| Sheep_DNase_I | -------- | SEQ ID NO.:6 |
| Pig_DNase_I | -------- | SEQ ID NO.:7 |
| Rat_DNase_I | -------- | SEQ ID NO.:8 |
| Mouse_DNase_I | -------- | SEQ ID NO.:9 |
| Human_DNase_I_precursor | -------- | SEQ ID NO.:10 |
| Rabbit_DNase_I | -------- | SEQ ID NO.:11 |
| LS-DNase | KKTKSKRS | SEQ ID NO.:12 |

\* — single, fully conserved residue
: — conservation of strong groups
. — conservation of weak groups
— no consensus Sequence Identity=78% Between sbDNase I and hDNase I The pZErO-2 vector served as the starting material for all downstream molecular biology manipulations. Two strategies were considered for expression in *E. coli:* 1) Compartmentalization, and 2) Inhibition of active DNase I. In the former, the DNase may be secreted to the periplasm after cellular translation and sequestered from chromosomal DNA. In the latter, the enzyme may be expressed in an inactive form and activated after the host cells are harvested. For example, the enzyme may be co-expressed with an inhibitor, such as actin, where the inhibitor is removed by a treatment that dissociates the inhibitor, or singularly expressed as inclusion bodies that can be refolded to active protein in a subsequent step.

Consequently, the synthetic bovine DNase I gene (sbD-Nase I) was subcloned into a variety of alternative vectors for purposes of overexpressing the protein in an *E. coli* host. Initially, PCR was performed using primers containing compatible restriction sites (AvaI and BamHI) to insert the sbDNase I gene into the vector pET-22b. This vector contains a pelB leader sequence that is known to trigger the secretion of some recombinant proteins into the periplasm following translation. Moreover, this vector also contains a T7lac promoter with adjacent lac operator sequence to provide tighter control over "leaky" expression. For toxic proteins such as DNase I, extremely tight control is essential to ensure the viability of the host cell. Indeed, when cloning of the sbDNase I gene into a vector containing a standard T7 promoter (pET-23b) was attempted, all "positive" clones identified by restriction digestion contained insertions or deletions near the ribosomal binding site that abolished target protein expression.

Roughly 1 ug of the pET-22b plasmid and 500 ng of the PCR product were serially digested with AvaI and BamHI and the gel-purified using a kit containing glass milk (Bio101). The linearized plasmid and PCR fragment were then ligated with T4 ligase using 70 ng of the plasmid and 35 ng of the PCR fragment. The ligation reaction (1 ul) was used to transform competent *E. coli* cells (TOP10 cells). Colonies were screened by both colony PCR and diagnostic restriction digests. Positive clones were confirmed by DNA sequencing to create pET-22b_sbDNase I. The coding sequence for the sbDNase I in this vector includes an additional 31 amino acids (MKYLLPTAAAGLLLLAAQPAMAMDIGINSDP (amino acids 1–31 of SEQ ID NO.: 4)) in the N-terminus that also contains the pelB secretion sequence (underlined sequence).

Expression of sbDNase I from pET-22b_sbDNase I was accomplished after transforming BL21(DE3), BL21(DE3) pLysS, or BL21(DE3)pLysE cells with vector and plating the transformed cells onto LB agar containing 50 ug/ml carbenicillin for growth at 37° C. overnight. A single colony was selected and added to 5 ml of LB with carbenicillin and incubated at 37° C. for 12–16 hrs, and 20–50 ul of the culture was used to seed 2 ml of LB media in a 15 ml test tube. Alternatively, one-quarter to one-half of the colonies were eluted from the plate directly into media to achieve an OD600 of 0.1. Once the OD600 reached 0.5–1.0, the cells were induced with 0.1–1 mM IPTG to activate expression from the T7lac promoter sbDNase I was successfully expressed from this vector; however, 97–99% of the recombinant protein was present in insoluble inclusion bodies in the cytoplasm. No active sbDNase I could be detected in the periplasm.

An alternative approach to targeting sbDNase I to the *E. coli* periplasm is to create a fusion protein with a host protein that localizes in the periplasm. The vector pET-40b presents an N-terminal protein sequence taken from the periplasmic *E. coli* protein DsbC. Fusions of sbDNase I and DsbC were created in plasmid maintenance *E. coli* strains such as DH5α. However, this construct could not be successfully transformed into *E. coli* strains containing a DE3 lysogen, presumably due to the toxicity of the fusion protein product. Since DsbC is a disulfide isomerase, the production of DsbC in a fusion with DNase I may have also triggered a more active, and thus toxic, DNase I.

sbDNase I containing the pelB leader sequence was also subcloned in pBAD, a plasmid that contains a tightly controlled arabinose-responsive promoter. However, the results using this vector were essentially the same as with pET-22b_sbDNase I: the vast majority of the expressed protein accumulated as inclusion bodies. FIG. 5 is a graph that shows a >20-fold increase in DNA cleaving activity when *E. coli* culture fluid is compared before and after sbDNase I induction Given the difficulty obtaining active, soluble sbDNase I, considerable effort was made to refold the cytoplasmic material expressed from pET-22b_sbDNase I. Strategies using gradual dialysis or shock dilution (10- to 100-fold dilution) into a variety of denaturants (guanidinium, arginine, sulfobetaines, etc., both with and without an active redox system, such as that which includes reduced and oxidized glutathione) were attempted. However, the protein is extremely susceptible to precipitation under these conditions, and enormous dilutive volumes were needed to counter this effect. Handling such large volumes is simply not practical. In general, only 1–5% of activity could be recovered in a best case.

Attempts to refold the sbDNase I from inclusion bodies while the protein was bound to a solid support (e.g., His-tagged sbDNase I bound to Ni-NTA or Co resin) were also unsuccessful. One problem with this approach was that the affinity tag on sbDNase I did not appear to bind tightly to the column affinity matrix. Much of the protein dissociated from the support over the timescale of the study.

Roughly 1–3% of the DNase I expressed from pET-22b_sbDNase I was soluble. Although some soluble, active protein could be recovered from the cells themselves, most of the soluble enzyme was present in the culture fluid. It may be that when protein expression is induced, some fraction of the nascent enzyme is expressed in an active, soluble form. This fraction may trigger a "pseudo-apoptotic" state in the *E. coli* host, whereby the cell dies and ruptures. Following lysis, the contents of the cells are emptied into the culture fluid where it can be harvested for purification of active sbDNase I. Using this strategy, a maximum of ~1 mg/L of soluble, active sbDNase I could be expressed.

Interestingly, pET-22b_sbDNase I could not be transformed into "Origami" strains of *E. coli* that contain a DE3 lysogen. Origami strains contain inactivating mutations in host redox proteins thioredoxin reductase and glutathione reductase. As a result of these mutations, the normally reducing environment of the cell cytoplasm is shifted to a more oxidizing state. Since DNase I contains 2 disulfide bonds, one of which (C173–C209) is known to be critical for activity, it may be that the more oxidizing environment of the Origami cells allows what little sbDNase I that may "leak" in the uninduced state to be much more active than that enzyme that may leak when the cytoplasm is highly reducing (as it is normally; i.e., in the case of expression of pET-22b_sbDNase I in BL21(DE3)). Thus, expression of DNase requires a delicate balance between minimally active leaky expression and maximal induced expression, where the former is necessary for cell viability, and the latter is required for optimal expression yields.

An alternative strategy for expression of active recombinant DNase I was described by Worrall and Connolly (Gene (1993) 136:337–40). In this case, expression of recombinant DNase I was induced after the infection of *E. coli* with λCE6, a phage engineered to contain the gene for T7 RNA polymerase. After infection, the T7 RNA polymerase drives transcription of the target gene, and recombinant protein is produced. This strategy was successful, but the yields were poor: 0.25–0.5 mg/L recombinant DNase I/L. This method may be undesirable because a large amount of λCE6 phage must be procured for large scale expression. This phage is time-consuming and costly to grow, harvest, and purify.

pET-22b_sbDNase I plasmid was transformed into either JM109 (λCE6 induction) or BL21(DE3) (IPTG induction) cells. When cells were induced with λCE6, JM109 cells containing the expression vector were grown in LB supplemented with 0.2% maltose to an OD600 of 0.6–1.5. MgSO$_4$ was added to a final concentration of 10 mM and λCE6 to 2–4×10$^9$ pfu/ml. Cells were grown for 3–16 hrs, and the culture fluid harvested. Induction of BL21(DE3) was accomplished at an OD600~0.6–1.0 using 0.5 mM IPTG. Assays were performed by adding 5 ul of culture fluid to a reaction at 37° C. containing 1×DNase I buffer and 200 nM DNaseAlert™ substrate. The fluorescent intensity, which increases as the substrate is cleaved, was monitored continuously using a SpectraMAX GeminiXS fluorescence microplate reader. In this assay, an initial velocity of 13.5 RFU/sec corresponds to 1 unit of activity.

TABLE 2

Activity of sbDNase I Overexpressed in *E. coli*.

| Sample | Inducer | Induction Time | Activity (units/ul culture fluid) |
|---|---|---|---|
| sbDNase I | λCE6 | 5 hrs | 0.015–0.03 Units/ul |
| sbDNase I | λCE6 | Overnight | 0.03 Units/ul |
| sbDNase I | IPTG | 4 hrs | 0.015–0.03 Units/ul |
| sbDNase I | IPTG | 8 hrs | 0.04–0.06 Units/ul |

EXAMPLE 2

Purification of sbDNase I from *E. coli*. The chromatographic strategy used to purify sbDNase I was based in part by that described by Chen et al. (Protein Science 2002; 11:659–668). Binding of sbDNase I to an anion exchange resin is mediated by its calcium binding properties. In addition to having several weak calcium binding sites, sbDNase I has two strong binding sites that bind with a micromolar $K_d$. A steric shift to binding free calcium and subsequent conformational change is likely to cause DNase to elute at low calcium concentrations (reportedly 7 mM), although the sbDNase I protein described herein elutes at a higher calcium concentration. Soluble sbDNase I collected from induced BL21(DE3) culture fluid was concentrated and dialyzed, in their case, by an ultrafiltration cell and purified by anion exchange. The sbDNase I activity was loaded onto the column in low ionic strength buffer (20 mM Tris pH 7.5), and eluted using a shallow CaCl$_2$ gradient (0–15 mM).

The sbDNase I sequence in the pET-22b host plasmid containing the pelB leader sequence was transformed and expressed according to the method outlined above. A 2 L batch of culture fluid was harvested after 8 hours of induction using 0.5 mM IPTG. Cells were pelleted at 3300×g and the supernatant was collected. A small precipitation study was done testing 40–80% ammonium sulfate precipitations to determine optimal precipitation of sbDNase I from the culture fluid, (>90% recovery at 60% ammonium sulfate).

On the basis of these results, the culture fluid (for example, 1 L) was precipitated using 60% ammonium sulfate (390 g), resuspended in 10 ml, and dialyzed against two changes of Q column buffer A (20 mM Tris pH 7.5). The ionic strength was confirmed to be roughly the same as buffer A and the sample loaded onto 5 ml prepacked HiTrap™ Q from Amersham Pharmacia equilibrated in buffer A. The column was eluted with a gradient of 0–100 mM CaCl$_2$. Peak sbDNase I activity was detected by DNaseAlert™ after elution at 30–40 mM CaCl$_2$. The purity of peak fractions was confirmed by SDS-PAGE and western blot revealed a major band around 30 kD that represents approximately 70% of the total protein by SDS-PAGE (data not shown). Since starting yields of sbDNase I yields are low, subsequent loss during purification would make this method cost prohibitive. This method was abandoned and efforts turned to sbDNase I expression in the yeast *Pichia pastoris*.

EXAMPLE 3

Expression of sbDNase I in *P. pastoris*. The sbDNase I gene was cloned into the pPICZαA expression vector (Invitrogen), which is a shuttle vector containing the Zeocin resistance marker and yeast alpha-mating factor secretion signal sequence. The following primers were designed using NotI and XhoI restriction sites for insertion into the pPicZalpha plasmid:

```
                sbDNase I sequence
     XhoI      L  K  I  A  A  F  N  I
ATCCGCTCGAGAAGAGACTGAAGATCGCAGCTTTCAACATC    (SEQ ID NO.: 13)
pPICZsbDNase-Forward
```

```
       NotI   StopT  L  T  V  E  V
ATAAGAATGCGGCCGCTTAAGTCAGGGTCACCTCAACCG      (SEQ ID NO.: 14)
pPICZsbDNase-Reverse
```

PAGE-purified primers were used to PCR amplify an ~800 bp fragment from pET-22b_sbDNase I. This ~800 bp fragment (~700 ng) was gel-purified, and digested with 50 U Not 1 and 20 U Xho I overnight. The pPicZαA vector (1.2 ug) was similarly digested. Both double-digested samples were then gel purified. FIGS. 3A and 3B show the nucleic and amino acid sequences, respectively, of the alpha mating factor fusion protein that contains a sequence optimized, recombinant sbDNase I gene of the present invention (SEQ ID NO.: 19 and SEQ ID NO.: 20, respectively). The sbDNase I gene (20 ng) and linearized vector (100 ng) were ligated using the Quick Ligation Kit (NEB). The ligated product (1 ul) was transformed into XL-1 Blue cells (Novagen) and plated out on Lennox L plates containing 30 ug/ml Zeocin antibiotic. Clones were prepared with the QIAprep Spin Miniprep Kit, screened by diagnostic restriction digests using Not I/Xho I and sequenced through the entire sbDNase I gene.

Expression of sbDNase I in *P. pastoris* was preformed using a method similar to that described in *Pichia Protocols* (Methods in Molecular Biology vol. 103, Humana Press). sbDNase I_pPICZαA plasmid (1.5 ug) was linearized with PME I and purified using a DNA Clean and Concentrator™-5 kit (Zymo Research Products). The linearized plasmid (0.5 ug) was transformed into electrocompetent *Pichia* X-33 cells via electroporation. Cells were plated out on YPD/Zeocin plates (100–2000 mg/L). Clones were screened by test expression in BMGY (growth phase) then induced in BMMY (1% methanol) for 24–46 hours. Enzyme activity in the culture fluid was monitored using the DNaseAlert™ fluorescence assay. DNase I activity corresponded to yields ranging from 7.5 to 18 mg/L compared to essentially no DNase I activity in the uninduced strain or the non-transformed control. Verification of samples by SDS-PAGE revealed a prominent double band around 30–34 kD.

sbDNase I expression conditions for growth in shake flasks were tested and scaled up for volumes 5 ml up to 1 L. Scaling of growth conditions was not problematic. Several parameters were optimized: 1) The rate of methanol addition during the induction phase was determined empirically to be optimal between 1–1.5% addition per 24 hours; 2) Increasing aeration of the culture by the use of baffled flasks with large head volume, and covering the top of the flask with cheesecloth improved yields from 7.5 mg/L to as much as 18 mg/L; 3) Addition of supplemental glycerol (1%) and biotin (IX) after 20–24 hours growth after which, cultures were allowed to continue grow for an additional 20 hours; and 4) Growth of sbDNase I_pPicZαA FM22 fermenter media was also tested and gave peak yields of 37 mg/L. This approach requires a significant hands-on attention when a digital controller unit is not used, as the pH needs frequent adjustment.

EXAMPLE 4

Purification of sbDNase expressed in *P. pastoris*. The purification protocol was easily scaled with one exception. Difficulty was encountered trying to precipitate expressed sbDNase I from BMMY culture fluid supernatant. Optimal precipitation yields were evaluated and, even at 70% ammonium sulfate, only 50% of the target protein was recovered from the precipitation. Thus, there can be variability in media formulations that can result in poor yields subsequent to ammonium sulfate precipitation. Membrane filtration and tangential flow concentration approaches enabled far better recovery of recombinant protein after concentration (>95%). A batch of 1860 ml of culture fluid was precipitated by slow addition of ammonium sulfate to 70% at 4° C. The precipitate sbDNase I was pelleted, resuspended, and dialyzed against Q column buffer A (10 mM Tris pH 7.5, 0.1 mM $CaCl_2$) until equilibrated. Calcium was included at a concentration of 0.1 mM to stabilize the protein during dialysis. The dialyzed sample was loaded onto a 5 ml HiTrap™ Q column from Amersham Pharmacia. The column was eluted with a gradient of 0–100 mM $CaCl_2$ and peak sbDNase I activity detected by DNaseAlert™ was represented as a prominent shoulder at 25–30 mM on the UV trace. Yields from this procedure were about 60%. SDS-PAGE analysis revealed a double band around 32 kD that represented ~95% of the total protein in the fraction pool.

The net surface charge of the sbDNase I molecule is −4 and −8 at pH 6 and 7, respectively, but there are pockets of positively-charged residues that bind well to cation exchange resin. These sites include the DNA binding pocket, which binds negative charges along the DNA phosphate backbone. To further purify the protein, fractions from the Q column were pooled and resolved on an HiTrap SP Sepharose (Amersham Pharmacia) cation exchange column. Peak fractions were dialyzed against SP column buffer A (20 mM HEPES pH 6.5, 1 mM $CaCl_2$) and loaded onto the SP column. The column was eluted with a 0–1 M NaCl gradient and maximal DNaseAlert™ activity eluted at ~300 mM NaCl. SDS-PAGE analysis revealed a doublet of 32 kD bands with no other visible protein contamination. In toto, the sbDNase I was recovered in roughly 50% yield after column chromatography. Peak fractions from the SP column run were dialyzed against DNase I storage buffer (20 mM HEPES pH 7.2, 10 mM $CaCl_2$, 10 mM $MgCl_2$, 1 mM DTT, 50% glycerol). An early study using this purification protocol was also tried using a different buffer system at pH 7.5 (10 mM Tris pH 7.5, 0.1 mM CaCl$_2$). About 40% of the sbDNase I was detected in the flowthrough consistent with the protein having a greater negative surface charge and decreased binding to the cation exchange column. Therefore, it was found that purification using this protocol is more robust with a lower pH.

EXAMPLE 5

Characterization of purified sbDNase I purified from *P. pastoris*. Purified sbDNase I appears as a doublet of 30 and 32 kDa bands after SDS-PAGE. These molecular weights were more precisely assessed by MALDI-TOF analysis, and found to be 30.5 and 32.5 kDa. It is well known that *P. pastoris* is capable of adding post-translational modifications such as carbohydrate extensions to expressed proteins. Thus, the difference in molecular weight in the two polypeptides may be reasonably ascribed to differences in glycosylation. To test for this possibility, sbDNase I expressed in *P. pastoris* was characterized using the Gelcode Glycoprotein Stain Kit (Pierce). This analysis revealed that the upper (slower moving) sbDNase I band was significantly more glycosylated that the lower (faster moving) band. Glycosylation is consistent with the reduced mobility of the upper band. A control sample of purified bovine DNase I, known to be glycosylated, also stained positive. A non-glycosylated sbDNase I expressed in *E. coli* migrated with the lower band of the doublet from *P. pastoris*. Neither of these bands was stained. DNA zymography, which reports the activity of nucleases after separation by SDS-PAGE, revealed that both the 30.5 kD and 32.5 kD bands are capable of cleaving double-stranded DNA.

Examples of other proteins that are toxic and that may be expressed using the present invention are listed in Table 3. The present invention may be used to expressed proteins that have varying degrees of toxicity in bacterial hosts, e.g., *E. coli*, and that have enzymatic or other activities that affect bacterial reproduction, gene transcription, translation, the integrity of DNA, RNA, proteins and other structural components of the host. The system disclosed herein permits improved and/or increased expression of the proteins listed below.

TABLE 3

Recombinant Proteins Toxic to *E. coli* expressable as recombinant proteins in *P. pastoris*

| | |
|---|---|
| DNase I | Ambion, unpublished |
| | DNA Cell Biol, Aug. 1, 1994; 13(8): 875–82. |
| RNase A | Ambion, unpublished |
| Honeybee Prepromelittin | Infect. Immun., November 2002; 70: 5924–5930. |
| Leptospira interrogans Lig A | Infect. Immun., December 1999; 67: 6510–6517. |
| Histone H1 Homologue (HupB) | EMBO J., September 1997; 16: 5235–5246. |
| RNA-binding protein domain (RBD 1 + 2) | J. Biol. Chem, August 1992; 267: 15932–15937. |
| Poliovirus nonstructural protein 3AB | Biochem Biophys Res Commun, November 1992; 188(3): 972–81. |
| Feline tumor necrosis factor | Clin. Diagn. Lab. Immunol., November 1995; 2: 740–746. |
| Centromere binding protein CENP-B | Biotechniques, May 1, 1997; 22(5): 798–800, 802. |
| Human apoptosis modulator protein Bax | Protein Expr Purif, August 2001; 22(3): 422–9. |
| TolAI-beta-lactamase fusion protein | Gene, Oct. 1, 1999; 238(2): 325–32. |
| DsbA'-PhoA fusion protein | J. Bacteriol., February 2001; 183: 1147–1158. |
| Neutral horseradish peroxidase, HRP-n | J Biotechnol, September 1994; 37(2): 133–42. |
| Pokeweed antiviral protein (PAP) | Biochimie, Dec. 1, 1998; 80(12): 1069–76. |
| Yeast plasma membrane ATPase, PMA1 | J. Biol. Chem, August 1989; 264: 14389–14395. |
| *E. coli* poly(A) polymerase (PAPI) | Mol Microbiol, June 2002; 44(5): 1287–98. |
| F-ATPase | J Mol Biol, Jul. 19, 1996; 260(3): 289–98. |
| Isoleucyl-tRNA synthetase | Gene, April 1994; 141(1): 103–8. |
| Yeast DNA polymerase delta | J. Biol. Chem, January 1993; 268: 982–990. |
| Human estrogen receptor alpha (hERalpha) | J Steroid Biochem Mol Biol, November 2000; 74(4): 169–78. |
| Bacteroides thetaiotaomicron pectin methylesterase and pectate lyase | Microbios, January 1999; 97(386): 39–53. |
| Yeast DNA repair protein Rad4 | Mutat Res, May 1998; 400(1–2): 127–33. |
| Antimicrobial peptide P2 | Biotechnol Bioeng, January 1998; 57(1): 55–61. |
| Pyrococcus furiosus DNA polymerase, Pfu | Protein Expr Purif, Nov. 1, 1997; 11(2): 179–84. |
| Human 2',5'-linked oligoadenylate-dependent RNase L | FEMS Microbiol Lett, April 1997; 149(1): 107–13. |
| Potato protease inhibitor PI2 | Biochim Biophys Acta, Jun. 20, 1995; 1267(2–3): 83–91. |
| *E. coli* Ffh protein | Biochim Biophys Acta, June 1995; 1267(2–3): 83–91. |
| Semliki Forest virus 6K protein | J. Biol. Chem, April 1994; 269(16): 12106–10. |
| Neisseria porin protein | Gotschlich et al., PNAS (1987) 8135–8139 |
| | Carbonetti and Sparling, PNAS 84 (1987) 9084–9088 |
| | Carbonetti et al., PNAS 85 (1988) 6841–6845 |
| Bacteriophage T7 gene 1.2 and gene 10 | J. Bacteriol., Feb. 1, 1991; 173(4): 1536–43. |

TABLE 3-continued

Recombinant Proteins Toxic to *E. coli* expressable as recombinant proteins in *P. pastoris*

| | |
|---|---|
| Rhizopus delemar lipase | Lipids, Feb. 1, 1993; 28(2): 81–8. |
| HIV protease | PNAS, July 1990; 87(14): 5573–7. |
| | Biomed Biochim Acta, January 1991; 50(4–6): 643–6. |
| Bacteriophage T4 nucleoid disruption (Ndd) | Mol Microbiol, May 1, 1996; 20(3): 519–28. |
| RNase T1 | Eur. J. Biochem., May 1988; 173(3): 617–22. |
| Human adenovirus type 2 fiber protein | Gene, Sep. 30, 1989; 81(2): 267–74. |

EXAMPLE 6

E13R DNase I mutant construction. Clone E13R_sbDNase I_pPICZαA was created using sbDNase I_pPICZαA as a template for PCR using the Quick Change mutagenesis kit (Stratagene). The PCR product was transformed and plated onto Lennox L plates containing Zeocin (30–100 ug/ml). Clones were prepared with the QIAprep Spin Miniprep Kit, screened by diagnostic restriction digest using Eag I/Xho I and sequenced through the entire sbDNase I gene. The sbDNase I mutants containing E13R and N74K were designed using the following sequences:

```
E13R Forward Primer containing Eag I silent mutation:
              ↓
CATCCGCACCTTCGGCCGTACCAAAATGTCCAACGCTACTC    (SEQ ID NO.: 15)
   I  R  T  F  G  R   T  K  M  S  N  A  T E13R Reverse Primer:
GAGTAGCGTTGGACATTTTGGTACGGCCGAAGGTGCGGATG    (SEQ ID NO.: 16)
```

Mutant E13R was transformed into *Pichia* X-33 competent cells. Plasmid (3 ug) was linearized with Pme I, purified using a DNA Clean and Concentrator™-5 kit (Zymo Research Products), electroporated into *Pichia* X-33 electrocompetent cells and plated as described previously for sbDNase I_pPICZαA. Clones were screened by test expression in BMGY/BMMY for 24–46 hours. Enzyme activity was measured in the culture fluid using DNaseAlert™.

EXAMPLE 7

Enzymatic properties of E13R sbDNase I. The salt tolerance of E13R sbDNase I was analyzed using DNaseAlert™. Upon addition of 150 mM NaCl, the mutant maintained 81% of its activity in low salt, whereas wild-type DNase I maintained only 6% activity. The E13R mutant still had 7% activity in 300 mM NaCl where wild-type DNase I was essentially inactive.

$K_m$ measurements were performed using DNaseAlert™. Since the sbDNase I protein completely dominates the small amount of background DNase activity in the culture fluid of *P. pastoris*, rigorous kinetic assessments of the enzyme can be conducted using unpurified enzyme from the culture fluid. The $K_m$ of the E13R sbDNase I was less than 100 nM, or about 5- to 7-fold lower than the $K_m$ of native bovine DNase I or sbDNase I.

EXAMPLE 8

Expression of E13R;N74K DNase I in *P. pastoris*. The hDNase I N74K mutant has been described as a more salt-tolerant, $V_{max}$ mutant. N74K sbDNase I was created as described above using the following primers:

```
N74K Forward Primer:
         ↓
GCCGCTGGCCGCAAGAGCTACAAAGAGCGC    (SEQ ID NO.: 17)
   P  L  G  R  K  S   Y  K N74K Reverse Primer:
CTTTGTAGCTCTTGCGGCCGAGCGGCTCGC    (SEQ ID NO.: 18)
```

The sbDNase I N74K mutant was expressed in *P. pastoris* according to the standard procedure. Characterization of the N74K sbDNase I mutant by DNaseAlert™ failed to demonstrate improved activity in higher salt compared to the wild-type DNase. In spite of this negative result, a double mutant of E13R;N74K sbDNase I was created and tested. Clone E13R;N74K_sbDNase I_pPICZαA was constructed using the N74K mutagenic primers, and E13R_sbDNase I_pPICZαA as a template for PCR using the Quick Change mutagenesis kit. The PCR product was transformed into XL-1 Blue cells and plated out on Lennox LB plates plus Zeocin (30–100 ug/ml). Clones were prepared with the QIAprep Spin Miniprep Kit, screened by diagnostic restriction digest using Eag I/Xho I and sequenced through the entire modified sbDNase I gene.

For transformation of the E13R;N74K sbDNase I plasmid into *P. pastoris*, the DNA was linearized with Pme I, purified using a DNA Clean and Concentrator™-5 kit (Zymo Research Products), electroporated into *Pichia* X-33 electrocompetent cells and plated as described previously for sbDNase I_pPICZαA. Clones were screened by test expression in BMGY/BMMY for 19–46 hours. Enzyme activity was measured in the culture fluid using DNaseAlert™. Glycerol stocks of were made by adding 20% Glycerol to BMGY culture. Stocks were stored at –80° C.

EXAMPLE 9

Optimization of E13R;N74K DNase I Expression in *P. pastoris*. Expression of the double mutant was easily scaled to preparative quantities. Colonies from E13R; N74K_sbDNase I_pPICZαA were picked and cultured in BMGY (5 ml to 4 L) for 40 hours. Next, the cells were pelleted and the media was exchanged to BMMY containing 1% methanol. The induction phase lasted 24–90 hours. Methanol was supplemented at a rate of 1–1.5% per 24 hours of induction.

Alternatives to the standard media components were evaluated to optimize the recovery of active enzyme. A MES-based buffer system (10 mM and 30 mM MES, pH 6.0) was tested to allow for free calcium ions on supplementation. Since $CaCl_2$ is known to stabilize DNase I in solution, addition of calcium was thought to minimize proteolysis and increase the specific activity of the product. Calcium readily forms a calcium phosphate precipitate in the presence of potassium phosphate ($K_{sp} \sim 10^{-33}$). For this reason, potassium phosphate buffer may not be preferred. Expression in MES, however, was poor compared to the standard media.

So-called minimal media, known as FM22 minimal media, was also evaluated in shake flasks. The FM22 media produced high yields of E13R;N74K sbDNase I. However, the pH was difficult to stabilize due to the lack of buffering capacity of this formulation. Expression temperature (25 or 30° C.) was also tested. These temperatures were equally effective in total yield, however, peak expression at 30° C. occurred at 40 hours. For cultures expressed at 25° C., yields climbed steadily to a maximum at 64 hours.

EXAMPLE 10

Purification of E13R;N74K sbDNase I from *P. pastoris*. A two column strategy was used for purification of E13R; N74K DNase I. Purification was most effective when cation exchange chromatography (HiTrap SP column) was performed before anion exchange (HiTrap Q). Culture fluid containing expressed E13R;N74K sbDNase I was concentrated by either ammonium sulfate precipitation or membrane filtration. As stated previously, yields from ammonium sulfate precipitation were poor (20–30% even when saturated with 90% ammonium sulfate) while membrane concentration worked well (>99% recovery). In each case, the concentrated sample was dialyzed against 20 mM HEPES pH 6.5, 1 mM $CaCl_2$ (HiTrap SP column buffer A) and loaded onto the HiTrap SP column. This column was eluted with Buffer A containing a 0–1M NaCl gradient and peak activity by DNaseAlert™ eluted at 450 mM NaCl. E13R; N74K sbDNase I was recovered from the column in roughly 75% yield.

Peak fractions were dialyzed against Q column buffer A (Tris pH 7.5, 0.1 mM $CaCl_2$) and loaded onto a 5 ml HiTrap Q (Amersham Pharmacia). The column was eluted with buffer A plus a gradient of 0–100 mM $CaCl_2$. Peak DNase activity detected by DNaseAlert™ was represented as a prominent shoulder at 25–30 mM on the UV trace. Samples from peak fractions run on 4–15% SDS-PAGE showed a major double band between 30 and 32 kD. Peak fractions from the Q column run were dialyzed against DNase I storage buffer (20 mM HEPES pH 7.2, 10 mM $CaCl_2$, 10 mM $MgCl_2$, 1 mM DTT and 50% glycerol) and stored at −20° C.

EXAMPLE 11

Enzymatic properties of E13R;N74K sbDNase I. The specific activity of the purified E13R;N74K sbDNase I mutant was measured using the industry standard lambda genomic DNA digestion assay and determined to be 300,000 U/mg. One unit is defined as the amount of enzyme required to completely degrade 1 ug of k DNA in 10 min at 37° C. in a buffer of 40 mM Tris-HCl, pH 7.9, 10 mM NaCl, 6 mM $MgCl_2$, 1 mM $CaCl_2$. Testing for residual RNase activity was conducted by overnight incubation of the enzyme with a radiolabeled RNA probe. Concentrations as high as 20 U/ul caused no significant degradation due to RNase contamination.

Figure 6A:
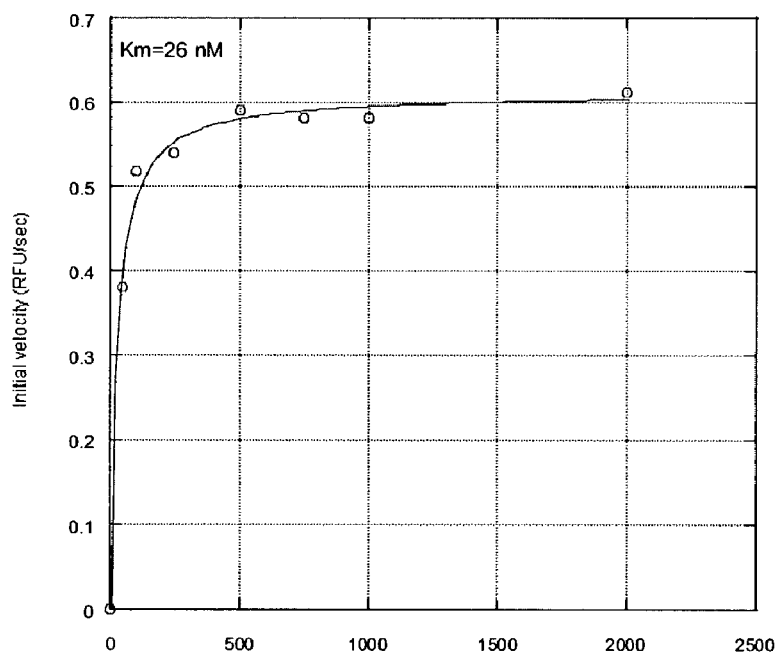
FIGS. 6A and 6B are graphs that compare the Km of E13R;N74K sbDNase I, against wild-type DNase I.
Figure 6B:
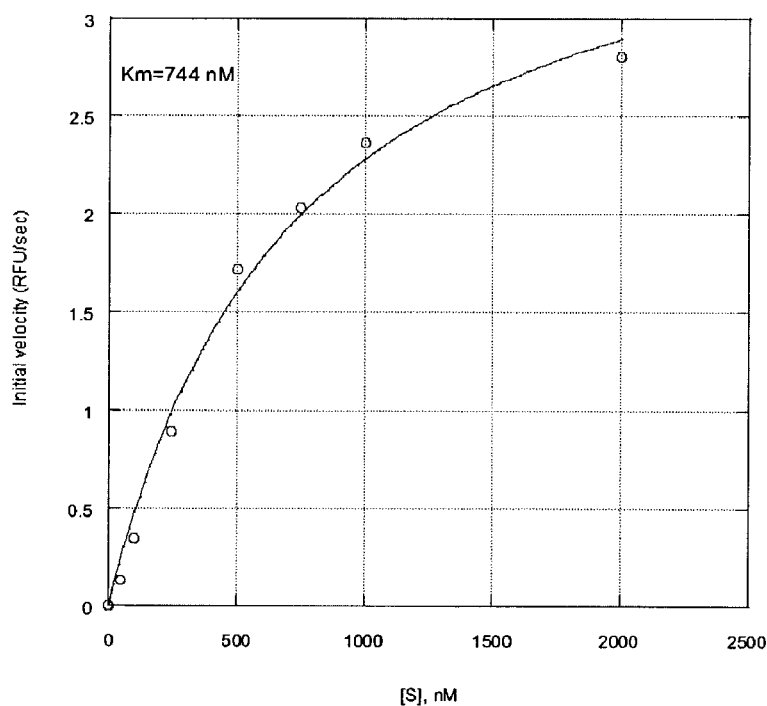

DNase activity of the E13R;N74K sbDNase I was tested with the DNaseAlert™ assay. The E13R;N74K sbDNase I manifested a pronounced tolerance to high salt concentration. The activity of E13R;N74K sbDNase I increased 3.6-fold in the presence of 150 mM NaCl compared to no added NaCl in a buffer containing 10 mM Tris (pH 7.5), 2.5 $MgCl_2$, 0.5 mM $CaCl_2$. At 300 mM NaCl, the double mutant was still active at 12% of its activity in no NaCl. As shown in FIG. 6, the $K_m$ of this enzyme was 26 nM, more than 20-fold lower than unmodified DNase I in the same buffer. The $K_m$ (and Vmax) increased with increasing salt; in a buffer with an ionic strength of 140 mM, the $K_m$ was 126 nM.

DNaseAlert™ was also used to compare the salt tolerance of E13R;N74K sbDNase I over a range of calcium concentrations. Tolerance for KCl was tested in parallel. Optimal NaCl and calcium concentration was determined to be 125 mM NaCl and 0.5 mM $CaCl_2$. This result was confirmed using the Lambda genomic DNA digestion assay.

Figure 7:
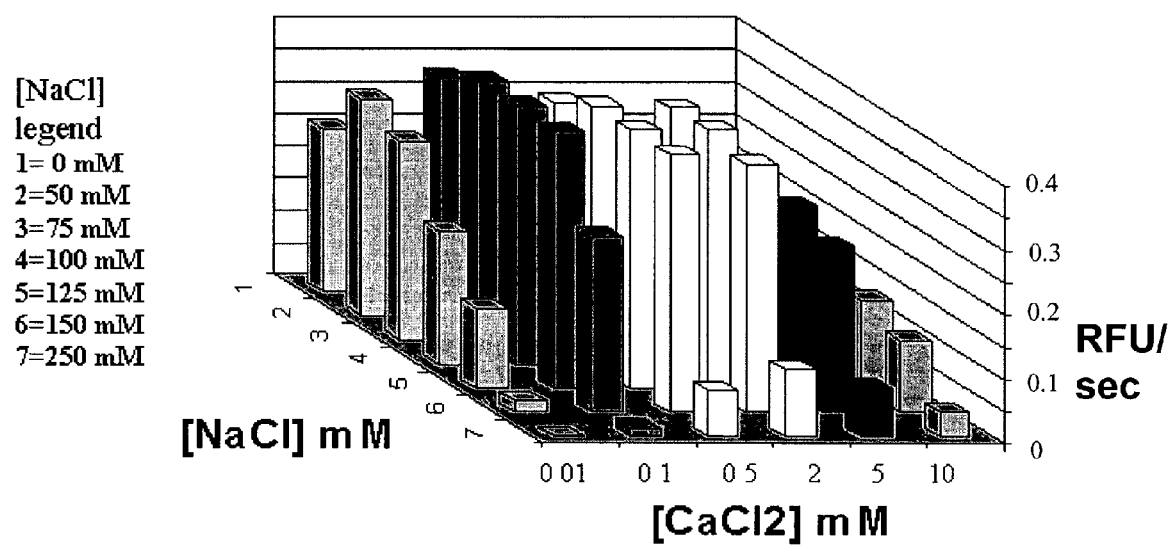
FIG. 7 is a three dimensional graph that shows the interrelationship between $Ca^{2+}$ and monovalent salt in modulating El 3R;N74K sbDNase I activity.

These results reveal that salt tolerance can be "ratcheted" upwards by increasing the calcium concentration. As seen along the z-axis in FIG. 7, the activity of E13R;N74K sbDNase I in higher concentrations of salt increases as the $CaCl_2$ is increased to a level of 2 mM where 15% maximum activity is preserved in 250 mM NaCl. By comparison, wild-type DNase I is reduced to 15% activity in 75 mM NaCl. Thus, the increased sensitivity of the enzyme to high salt in low concentrations of calcium serves as a "switch" to turn the enzyme activity on or off. Although E13R;N74K sbDNase I was less active when KCl was used as the monovalent salt, the trend for calcium-dependent salt tolerance was identical, and may also be used with the present invention.

EXAMPLE 12

Removal of DNA prior to RT-PCR. DNase I is the tool of choice for removing contaminating DNA from RNA preparations. The need to remove DNA is particularly acute for PCR-based applications that can detect nucleic acid at zeptomole levels. RNA suitable for use in the system and method disclosed herein may be contained in a biological sample suspected of containing a specific target RNA. The biological sample may be a heterogeneous sample in which RNA is a small portion of the sample, as in for example, a whole organ, a tissue from an organ or even a tissue biopsy.

RNA is prepared by any number of methods; the choice may depend on the source of the sample and availability. Methods for preparing RNA are described in, e.g., Davis et al., 1986, Basic Methods in Molecular Biology, Elsevier, N.Y., Chapter 11; Ausubel et al., 1987, Current Protocols in Molecular Biology, Chapter 4, John Wiley and Sons, NY; Kawasaki and Wang, 1989, PCR Technology, ed. Erlich, Stockton Press NY; Kawasaki, 1990, PCR Protocol: A Guide to Methods and Applications, Innis et al. eds. Academic Press, San Diego; and Wang and Mark, 1990, PCR Protocols: A Guide to Methods and Applications, Innis et al. eds. Academic Press, San Diego; relevant portions of which are incorporated herein by reference.

In operation, the RNA is isolated from whole organ, e.g., spleen. The resulting RNA molecule, referred to as total cellular RNA, may be purified to obtain mRNA using an oligo(dT) chromatography column (see e.g., U.S. Pat. No. 5,219,727, issued to Wang, et al., relevant portions incorporated herein by reference). The first step of the reverse-transcriptase-PCR method requires that the RNA template is combined with a suitable primer. An oligonucleotide is added to the reaction that acts as a point of initiation of DNA synthesis when annealed to the RNA template under conditions in which synthesis of a primer extension product is initiated, i.e., in the presence of four different nucleoside triphosphates. An appropriate buffer ("buffer" includes pH, ionic strength, cofactors, etc.) and at a suitable temperature are used to maximize the formation of single stranded cDNA. The primer may be, e.g., an oligodeoxyribonucleotide such as oligo(dT) that will initiate a single stranded DNA from all mRNA templates, although oligonucleotides with specific primer sequences or pools of oligonucleotides may be used to prime the reaction. A primer that includes a sequence sufficiently complementary to a specific RNA target molecule may used to prime synthesis of the first cDNA strand complementary to a specific target RNA segment if present. The primer is generally of sufficient length to prime the synthesis of extension products in the presence of the reverse transcriptase enzyme. When using oligo(dT), the primer hybridizes to the polyadenylation (polyA) sequence of mRNAs and provides a primer for cDNA synthesis from a heterogeneous population of mRNAs. Because most eukaryotic mRNA molecules contain a polyA sequence at the 3' end, an oligo(dT) primer has general utility in the present methods, for example, in the preparation of a cDNA library.

The primer typically contains 10–35 nucleotides, although that exact number is not critical to the successful application. Short primer molecules generally require lower temperatures to form sufficiently stable hybrid complexes with the template. For oligo(dT), a primer 16–21 nucleotides in length is suitable for high temperature cDNA, however, it may be preferable to provide an initial incubation at suboptimal temperature to elongate the oligo(dT) primer to provide enhanced stability of the primer-template duplex. Synthetic oligonucleotides may be prepared using, e.g., automated synthesis on a Biosearch 8700 DNA Synthesizer using phosphoramidite chemistry. The cDNA made in the RT reaction may then be stored or may be used in a polymerase chain reaction. The present invention finds particular utility when the RNA source may be contaminated with endogenous (or even exogenous) DNA that would cause a false positive in an amplification reaction.

The amplification of the single stranded DNA template that is made by reverse transcriptase if then used in a polymerase chain reaction mixture using, e.g., a thermostable polymerase. Thermostable polymerases are enzymes that are heat stable or heat resistant and catalyze polymerization of deoxyribonucleotides to form primer extension products that are complementary to a template nucleic acid strand. For continued cycling without the need to add more polymerase after each cycling step, thermostable DNA polymerases are used. A thermostable DNA polymerase will not irreversibly denature at about 90° and 100° C. under polymerization conditions.

The heating conditions for the repeated cycles of the polymerase chain reaction will depend on the buffer, salt concentration, and nucleic acids being denatured. As the product of the reverse transcription of mRNA is generally single-stranded, a high temperature denaturation step is unnecessary. RNA that forms secondary structures, e.g., stem and loop structures, may require a denaturation step in order to provide a suitable template for the reverse transcription and amplification. Following an initial denaturation or strand-separation step a first cycle of primer elongation provides a double-stranded template suitable for denaturation and amplification as referred to above. Temperatures at which specific nucleic acid denaturation occurs ranges from about 90° to about 105° C. The time required for at least partial denaturation to occur depends on the nucleic acid length, base content, and complementarity between single-strand sequences present in the sample, but typically about 0.3 to 4 minutes.

The thermostable or thermoactive DNA polymerases generally have an optimum activity at a temperature higher than about 40 degrees and generally between about 60° and 80° C. For example, AMV-RT has maximum activity at about 50 degrees C., but in order to maximize the efficiency and half-life of the enzyme, reactions using AMV-RT are generally carried out at about 43° C. Hybridization of the primer and template also depend on salt concentration, sequence composition and length of primer.

DNA amplification procedures by PCR are well known and are described in U.S. Pat. No. 4,683,202, relevant portions incorporated herein by reference. PCR requires two primers that hybridize with the double-stranded target nucleic acid sequence to be amplified. In PCR, double-stranded target sequences are denatured and one primer is annealed to each strand of the denatured target. The primers that anneal to the target nucleic acid are orientated such that the extension product of one primer, when separated from its complement, can hybridize to the other primer. Once a given primer hybridizes to the target sequence, the primer is extended by the action of the DNA polymerase. The DNA polymerase extension product is then denatured from the target sequence, and the process is repeated.

In successive cycles of this process, the extension products produced in earlier cycles serve as templates for subsequent DNA synthesis and using the appropriate amount of enzyme the rate-limiting step becomes the rate of polymerization. In the second and subsequent cycles, the product of amplification begins to accumulate at a logarithmic rate, thereby amplifying a large enough amount of the target sequence for cloning.

Cloning of the amplified fragments may be achieved by blunt ending the PCR fragments, by incorporating restriction enzyme sequence(s) into the primers, using known restriction sites or by taking advantage of the addition of an extra dA at the ends of the PCR product. The fragments may be sequenced directly or cloned into DNA vectors that permit propagation of amplified fragment.

As demonstrated herein, the E13R;N74K sbDNase I is more effective than wild-type DNase I in digesting DNA as measured by real-time PCR. RNA was isolated from three Mouse Spleens (Pel-Freez) using RNAqueous column purification following the manufacturer's instructions (Ambion). Briefly, a stock of 690 ng/ul total nucleic acid was obtained. DNase digestion was performed with 3.45 ug of nucleic acid in a volume of 60 ul containing either 2.4 U of wild-type DNase I in 1×DNase I buffer (10 mM TrisCl (pH 7.5), 2.5 mM $MgCl_2$, 0.5 mM $CaCl_2$) or E13R;N74K sbDNase I in 1×E13R;N74K sbDNase I buffer (10 mM TrisCl (pH 7.5), 100 mM NaCl, 2.5 mM $MgCl_2$, 0.5 mM $CaCl_2$) for 2–30 min. Aliquots (15 ul) were removed at each time point at heat treated at 95° C. for 5 min to inactivate the DNase. A portion of this aliquot (5 ul) was added to a one-step real-time mock RT-PCR reaction containing 0.4 uM primers, 80 nM TaqMan probe, 50 mM TrisCl (pH 8.3), 3 mM $MgCl_2$, 75 mM KCl, 0.4 mM dNTPs (each), 1×ROX internal dye, and 1 U SuperTaq. Cycling parameters were: 1)

Figure 9:
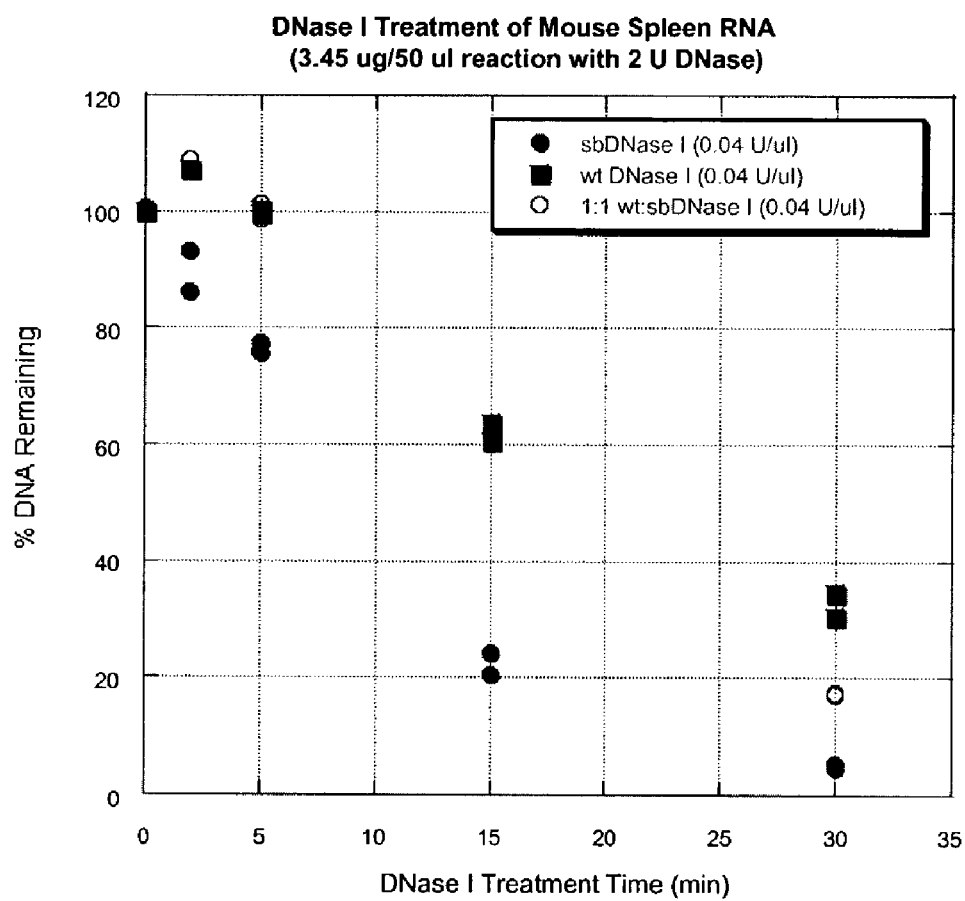
FIG. 9 is a graph that demonstrates the residual DNA contamination remaining as a function of time using E13R; N74K DNase I, a 1:1 blend of E13R;N74K DNase I and wild-type DNase I alone.

42° C., 15 min; 2) 95° C., 5 min; 3) 40 cycles of 95° C., 15 sec; 60° C., 1 min. As summarized in T shown in FIG. 9, the E13R;N74K sbDNase I clears DNA more efficiently than wild-type DNase I using RNA isolated from a mouse spleen, an organ that is a notoriously rich source of contaminating genomic DNA. It was found that after a 30 min incubation, the E13R;N74K sbDNase I-treated sample contains 5% residual contaminating DNA, whereas the wild-type DNase I-treated sample contains nearly 7 times as much.

TABLE 4 presents the residual DNA contamination remaining as a function of time.

| | Digestion Time | | | |
|---|---|---|---|---|
| | 2 min | 5 min | 15 min | 30 min |
| E13R; N74K DNase I (0.04 U/ul) | 89.8 | 76.6 | 22.3 | 5.0 |
| 1:1 Blend of E13R; N74K DNase I (0.04 U/ul) | >99.9 | 99.9 | 60.2 | 17.4 |
| wild-type DNase I (0.04 U/ul) | >99.9 | 99.8 | 62.3 | 32.5 |

EXAMPLE 13

Removal of DNA from Common Molecular Biology Buffers. Wild-type DNase I is limited by an absolute requirement for calcium ions and a pronounced sensitivity to modest to high salt concentrations. As a result, the wild-type DNase I enzyme requires a special buffer to effectively clear DNA. The E13R;N74K sbDNase I, in contrast, is much more calcium-independent and demonstrates an increase in activity as the salt concentration is increased. As a result, the E13R;N74K sbDNase I can be used with great flexibility, as DNA digestion does not necessarily require a dedicated buffer.

To demonstrate the broad range of activity, E13R;N74K sbDNase I was used in reactions (100 ul) containing 200 nM DNaseAlert™ substrate (Ambion) and 1×Buffer were pre-incubated at 37° C. in a SpectraMAX GeminiXS fluorescence microplate reader. After collecting a stable baseline using ex/em 535/556 nm, reactions were initiated with 0.1 U of wild-type DNase I or E13R;N74K sbDNase I (~65 pM final). The initial slope (RFU/sec) was recorded as a measure of the velocity of the reaction. Table 5 shows the percent of activity that is maintained compared to activity in the standard 1×DNase I buffer (10 mM Tris-HCl (pH 7.5), 2.5 MgCl$_2$, 0.5 mM CaCl$_2$).

TABLE 5

E13R; N74K sbDNase I Activity in Various Molecular Biology Buffers

| | % Activity in Common Buffers | | |
|---|---|---|---|
| | Wild-type DNase I | E13R; N74K sbDNase I | 1:1 Blend of E13R; N74K sbDNase I and wild-type DNase I |
| 1 × DNase I Buffer | 100 | 100 | 100 |
| RT buffer | 0.6 | 23 (38)* | 9 (15) |
| PCR buffer | 0.8 | 114 (143) | 44 (55) |
| Buffer A** | 0.1 | 58 (580) | 27 (270) |
| Buffer B*** | 1.4 | 205 (146) | 88 (63) |

TABLE 5-continued

E13R; N74K sbDNase I Activity in Various Molecular Biology Buffers

| | % Activity in Common Buffers | | |
|---|---|---|---|
| | Wild-type DNase I | E13R; N74K sbDNase I | 1:1 Blend of E13R; N74K sbDNase I and wild-type DNase I |
| PBS (+5 mM MgCl$_2$) | 0.005 | 16.7 (>100) | 7 (>100) |

*Values in parenthesis show the fold improvement in activity over wild-type bovine DNase I. Note that % activity levels of <1% are difficult to measure with great accuracy.
**Buffer A 1 × concentration: 50 mM Tris-HCl, 10 mM MgCl$_2$, 100 mM NaCl and 1 mM DTT (pH 7.9 at 25° C).
***Buffer B 1 × concentration: 20 mM Tris-acetate, 10 mM magnesium acetate, 50 mM potassium acetate and 1 mM DTT (pH 7.9 at 25° C.).

EXAMPLE 14

Figure 8:
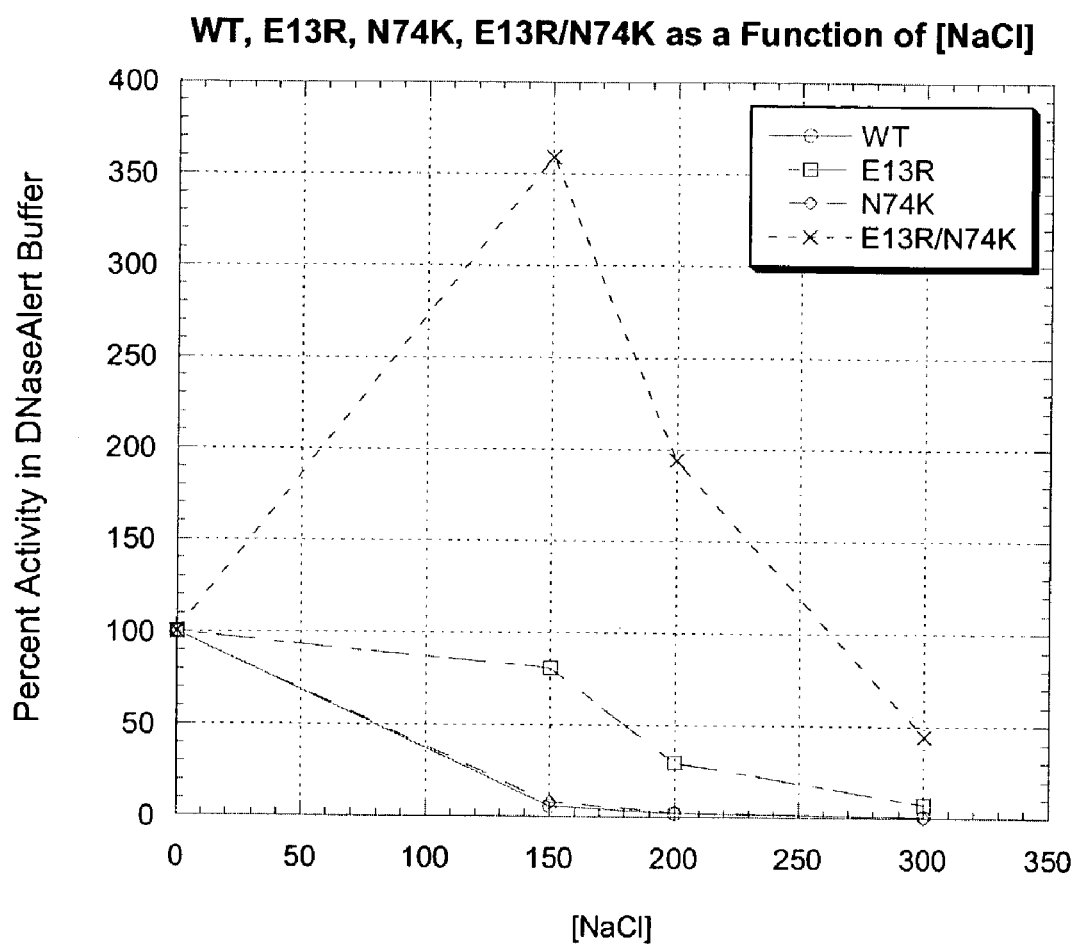
FIG. 8 is a graph that compares the salt tolerance of E13R, N74K, E13R;N74K, and wild-type DNase I in DNaseAlert Buffer.

Removal of DNA from an in vitro Transcription Buffer. Synthesis of RNA by in vitro transcription (IVT) requires a plasmid DNA template. This DNA template must be removed for many PCR-based applications. Typically, wild-type DNase I is used to digest the DNA. However, the high concentration of Mg$^{2+}$ in the transcription buffer is extremely inhibitory to DNase I. As summarized in Table 6 and FIG. 8, it was found that the salt-tolerant properties of the E13R;N74K sbDNase I enabled excellent DNA cleaving activity in this buffer; also shown are the activities of other mutants of the present invention. In fact, this activity is nearly as potent as the activity of the wild-type DNase I in its optimal 1×DNase I buffer. Either wild-type DNase I or E13R;N74K sbDNase I (1 ul of 0.1 U/ul) was added to a 9 ul reaction volume containing 1×IVT buffer and 1 ug of λ genomic DNA. The reaction was incubated for 20 min at room temperature (23° C.), and quenched with 10 mM EDTA. The DNA was resolved on a 1% agarose gel containing 1 ug/ml ethidium bromide.

TABLE 6

The superior activity of E13R; N74K DNase I DNA digestion compared to wild-type DNase I in in vitro transcription buffer.

| | Buffer | % residual DNA | Fragment size |
|---|---|---|---|
| Undigested Lambda DNA | | 100 | 50 kb |
| WT | DNase I | 1 | 0.1 kb |
| WT | IVT | 98 | 10 kb |
| E13R; N74K | IVT | 1 | 0.1 kb |

EXAMPLE 15

Simultaneous DNA cleavage and Reverse Transcription. RT-PCR is a common molecular biology procedure that typically requires DNA-free RNA. DNase I digestion of contaminating DNA is the method of choice for eradicating DNA in RNA preparations destined for reverse transcription and PCR. Currently, DNase treatment is performed in a step prior to RT-PCR, rather than in parallel with the reverse transcription step. There are two major reasons for this serial procedure: 1) wild-type DNase I has very little activity in RT buffer, and 2) the presence of active DNase in the reverse transcription step is generally believed to reduce the cDNA yield significantly by cleaving the primers or the nascent cDNA. The ability of the E13R;N74K sbDNase I to maintain activity in many molecular biology buffers provides a solution to the first problem. The second concern may be less significant as it is known that DNase I has <1% activity against ssDNA, or DNA:RNA hybrids. It may be possible to use a modest concentration of the E13R;N74K sbDNase I to provide sufficient DNA cleaving activity to remove offending dsDNA during reverse transcription without unnecessarily digesting the primers, cDNA, or, in the case of one-step RT-PCR using TaqMan probes, fluorogenic probes.

A simultaneous DNase digestion and reverse transcriptase reaction was assembled as follows. E13R;N74K sbDNase 1 (0.2–1.0 U) was added to a one-step real-time RT-PCR reaction containing 0.8 uM primers, 160 nM TaqMan probe, 50 mM TrisCl (pH 8.3), 3 mM $MgCl_2$, 75 mM KCl, 0.4 mM dNTPs (each), 1×ROX internal dye, 10 U MMLV RT RNase $H^+$ or 10 U of SuperScript II (SSII) RNase $H^-$, and 1 U SuperTaq. When DNA was added, 100 ng of human genome DNA (ATCC) was used. When RNA was added, HeLa-S3 total RNA (Ambion) was used. Cycling parameters were: 1) 42° C., 15 min; 2) 95° C., 5 min; 3) 40 cycles of 95° C., 15 sec; 60° C., 1 min.

As shown in Table 7, use of an RNase $H^-$ RT allows concurrent DNA digestion and reverse transcription, with a complete loss in DNA signal but a still significant RNA signal. The benefit of the RNase $H^-$ RT is thought to be due to the ability of non-degraded RNA template to hybridize to nascent cDNA and "lock" this cDNA into an RNA-DNA duplex. As such, formation of secondary structures in the cDNA that might be substrates for DNase I cleavage are avoided.

TABLE 7

Simultaneous DNase I Digestion and Reverse Transcription

| Nucleic Acid | RT | E13R; N74K DNase I (Units) | $C_t$ | $C_t$ Shift |
|---|---|---|---|---|
| HelaS3 RNA 1 ng | MMLV | 0 | 21.0 | |
| | | 0.2 | 27.5 | 6.5 |
| | | 0.5 | 30.5 | 9.5 |
| | | 1 | 36.0 | 15 |
| HelaS3 RNA 1 ng | SS II | 0 | 21.7 | |
| | | 0.2 | 24.8 | 3.1 |
| | | 0.5 | 26.3 | 4.6 |
| | | 1 | 28.7 | 7 |
| DNA 100 ng | SS II | 0 | 21.5 | |
| | | 0.2 | undet. | |
| | | 0.5 | undet. | |
| | | 1 | undet. | |

Wild-type DNase I cannot remove DNA in reverse transcription at reasonable concentrations. Similar studies performed with the wild-type DNase I enzyme reveal that the addition of 1 U to an RT minus, one-step RT-PCR reaction containing significant amounts of contaminating DNA shifted the signal by 0.5–1.3 Ct's, or only 1.4 to 2.5-fold. By comparison, the E13R;N74K sbDNase I reduced the DNA contamination by at least 1000-fold under the same conditions.

EXAMPLE 16

Compatibility of DNase I digestion with downstream applications such as RT-PCR is essential for accurate and sensitive RNA quantification. In this respect, the salt-stimulated properties of the E13R;N74K DNase I enzyme are problematic; optimal activity occurs in reaction buffers containing 100–150 mM NaCl. While passage of this salt into a reverse transcription is not inhibitory, salt carry-over to the PCR step is extremely inhibitory. As little as 30 mM additional NaCl to typical PCR buffers can reduce detection sensitivity in PCR by 5–10-fold when Taq polymerase is used. Addition of 40 mM NaCl completely eliminates activity. Moreover, even an extra 20 mM NaCl can scatter the data when detection is performed at or near the limit of detection. Since "one-step" RT-PCR reactions are by far the most popular RT-PCR format, an approach is required that limits the salt-inhibition of Taq polymerase in the PCR step.

The present inventors recognized that the activity of the sbDNase I enzymes of the present invention depended on total ionic strength of the solution, rather than the concentration of NaCl per se, which stimulates E13R;N74K DNase I activity provided a much-needed solution to this problem. Although all ions are not equally potent in enhancing E13R;N74K DNase I activity (e.g., KCl is only ~50% as stimulatory as NaCl), $MgCl_2$ is a powerful activator on par with NaCl. Consequently, a 1×E13R;N74K DNase I reaction buffer was developed that contained 50 mM NaCl and 10 mM $MgCl_2$. E13R;N74K DNase I activity in this buffer is comparable to that containing 100 mM NaCl, even though the concentration of NaCl is reduced by one-half. Consequently, one-half as much NaCl is passed into the RT-PCR thereby allowing a greater fraction of the DNase-treated sample to be analyzed without inhibition of the PCR step. Last, the residual $Mg^{2+}$ can be removed by simple batch resin treatment, as described in Example 17.

EXAMPLE 17

Streamlined Inactivation of DNase I. Current protocols that use DNase I usually require that the enzyme be inactivated or removed prior to downstream reactions. Common approaches include phenol:chloroform extraction followed by ethanol precipitation, or thermal denaturation at 65–75° C. for 10–20 min. Extraction, however, is tedious, requires extensive sample handling and can result in loss of RNA yield after precipitation. Heat inactivation, though simple to perform, can jeopardize the integrity of the RNA if performed in the presence of divalent ions. Another approach is to use a chelator such as EDTA, EGTA, BAPTA, or a chelating resin such as Chelex or BioRex-70. This general approach has been documented in the literature (Price, et al.), however, this strategy has not been linked to efficient, downstream reverse transcriptase reactions. By way of example, EGTA can be used to effectively inactivate wild-type DNase I or E13R;N74K sbDNase I prior to reverse transcription. In the case of wild-type DNase I, this inactivation is successful because the unmodified enzyme maintains very little activity in a typical RT buffer. For E13R; N74K sbDNase I, the absence of $Ca^{2+}$ after chelation causes the enzyme to become quite sensitive to salt, and thus poorly active in RT buffer. In addition, EGTA at a concentration below that of free $Mg^{2+}$ can be included in the RT buffer itself to allow an aliquot of the DNase I reaction to be passed directly into RT, thereby permitting for rapid, single-step RT-PCR without the need to extract the enzyme from the template source.

Effects of EGTA on real-time RT-PCR were evaluated in the following way. E13R;N74K sbDNase I (0.1–1 U) was added to a one-step real-time RT-PCR reaction containing 0.8 uM primers, 160 nM TaqMan probe, 50 mM TrisCl (pH 8.3), 3 mM $MgCl_2$, 75 mM KCl, 0.4 mM dNTPs (each), 1×ROX internal dye, 10 U MMLV RT RNase $H^+$, and 1 U SuperTaq. When DNA was added, 100 ng of human genome DNA (ATCC) was used. When RNA was added, HeLa-S3 total RNA (Ambion) was used. EGTA was added at a final concentration of 1 mM, or ~1.8-fold excess above the concentration of added $Ca^{2+}$. Cycling parameters were: 1) 42° C., 15 min; 2) 95° C., 5 min; 3) 40 cycles of 95° C., 15 sec; 60° C., 1 min. As shown in Table 8, the residual ~0.45 mM EGTA had no untoward effects on the efficiency of real-time RT-PCR, but completely inhibited E13R;N74K sbDNase I activity.

TABLE 8

Solution inactivation of E13R;
N74K sbDNase I prior to RT-PCR

| Condition | E13R; N74K sbDNase I (Units) | $C_t$ |
|---|---|---|
| 100 ng hGenomic DNA | 0 U | 21.6 |
|  | 0.1 U | 24.8 |
|  | 1 U | undet. |
| 100 ng hGenomic DNA + 1 mM EGTA | 1 U | 22.0 |
| 500 ng Hela S3 RNA | 0 U | 13.5 |
| 500 ng Hela S3 RNA + 1 mM EGTA | 1 U | 13.4 |

EXAMPLE 18

Streamlined Removal and/or Isolation of DNase I. An alternative to inactivation of DNase is to physically remove the DNase I. Based on the chromatographic properties of sbDNase I (see above), a sulfopropyl (SP) resin was selected. This cation exchange resin binds sbDNase I protein nearly quantitatively at pH<6, and can also remove divalent ions and partially desalt the sample. For maximal ease of use, the resin (1–15 ul of a 67% slurry) is added in batch to solutions containing sbDNase I at 1–5 U/50 ul for 1–2 min. The sample is then centrifuged at 10,000×g for 1 min, and the supernatant recovered for analysis.

The E13R;N74K sbDNase I was isolated by Sulfopropyl (SP) resin (Amersham). E13R;N74K sbDNase I (2 U) was added to 50 ul 1×E13R;N74K sbDNase I Buffer and treated with 5 ul of 67% SP Sepharose High Performance (HP) resin buffered in 50 mM Citric Acid pH 5.0. The samples were incubated for 5 min at room temperature with occasional mixing, and the resin pelleted at 10,000×g for 2 min. An aliquot (10 ul) of the supernatant was removed and added to a 20 ul reaction containing 1 ug of λ DNA in 40 mM Tris-HCl, pH 7.9, 10 mM NaCl, 6 mM $MgCl_2$, 1 mM $CaCl_2$. The sample was incubated at 37° C. for 10 minutes. This study demonstrated that greater than 98% of E13R;N74K sbDNase I was removed/isolated with a batch application of the SP resin under these conditions.

sbDNase I activity after divalent ion removal was evaluated. The SP resin removed >95% of the E13R;N74K sbDNase I activity, and, separately, >99% of the divalent cations required for activity. In this case, E13R;N74K sbDNase I (2 U) was added to 50 ul 1×E13R;N74K sbDNase I Buffer and treated with 5 ul of Ambion's DNA-free resin. This resin is known to remove divalent ions, but, under the conditions of this study, it only removed ~50% of the DNase I. A 67% SP Sepharose High Performance (HP) resin buffered in 50 mM Citric Acid pH 5.0, 1 ug λ DNA, and 500 mM Tris-HCl pH 8.0 (to adjust pH to an optimum range for potential sbDNase I activity) was incubated at 37° C. for 10 minutes. This example demonstrates the necessary removal of divalents to prevent RNA degradation when heated. The 15 ul reaction included 5 ul from the HP resin treatment of sbDNase I (~0.012 U/ul final), and 6.5 ul from the DNA-free treated 1×sbDNase I Buffer.

The present invention was used to produce a number of constructs for the expression of a protein that is highly toxic to E. coli, DNase I. Table 9 is a summary of some of the constructs that were designed, built and used to test expression and activity of the recombinant sbDNase I protein.

TABLE 9

Summary of Expression of sbDNase I in E. coli and Yeast

|  | Toxicity in E. coli | Soluble Overexpression in E. coli | Soluble Overexpression in Yeast | Activity in Low Salt | Activity in High Salt |
|---|---|---|---|---|---|
| pET-40b_sbDNase I* | +++ | NA | NA | NA | NA |
| pET-15b_sbDNase I | +++ | NA | NA | NA | NA |
| pET-23b_sbDNase I | +++ | NA | NA | NA | NA |
| pET-22b_sbDNase I** | − | + | NA | +++ | + |
| pBAD/gIII_sbDNase I*** | − | − | NA | NA | NA |
| pPicZαA_sbDNase I | NA | NA | +++ | +++ | + |
| pPicZαA_E13R_sbDNase I | NA | NA | +++ | ++ | ++ |
| pPicZαA_N74K_sbDNase I | NA | NA | +++ | +++ | + |
| pPicZαA_E13R;N74K_sbDNase I | NA | NA | +++ | ++ | +++ | where
− = no potency;
+ = low potency;
++ = medium potency;
+++ = high potency;
NA = Not Applicable.
*Contains a DsbC fusion sequence for export to the periplasm
**Contains a pelB leader sequence
***Contains a gene III leader sequence While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. An isolated and purified nucleic acid comprising a nucleic acid encoding the protein of SEQ ID NO: 2 for a DNase I.

2. The nucleic acid of claim 1, further comprising a synthetic nucleic acid sequence optimized for microbial expression.

3. The nucleic acid of claim 1, wherein the DNase I comprises a synthetic bovine DNase I further comprising an E13R mutation.

4. The nucleic acid of claim 1, wherein the DNase I comprises a synthetic bovine DNase I further comprising an N74K mutation.

5. The nucleic acid of claim 1, wherein the DNase I comprises a synthetic bovine DNase I further comprising an E13R mutation and an N74K mutation.

6. The nucleic acid of claim 1, wherein the nucleic acid further comprises a nucleic acid segment encoding a leader sequence.

7. The nucleic acid of claim 1, wherein the nucleic acid comprises a nucleic acid segment encoding an alpha mating factor leader sequence.

8. The nucleic acid of claim 1, wherein the nucleic acid comprises a codon-optimized bovine DNase I nucleic acid encoding SEQ ID NO: 2.

9. The nucleic acid of claim 1, wherein the protein encoded by the nucleic acid comprises an about 95 percent identity of higher with a codon-optimized bovine DNase I of SEQ ID NO: 2.

10. An expression vector comprising a nucleic acid encoding the protein of SEQ ID NO: 2 for a DNase I operably linked to a promoter recognized by a host cell transformed with the vector.

11. The expression vector of claim 10, wherein the host cell is a yeast cell.

12. The expression vector of claim 10, wherein the host cell comprises *Pichia pastoris*.

13. An isolated and purified nucleic acid comprising a nucleic acid sequence encoding a protein of at least about a 95% identity with a nucleic acid sequence encoding the protein of SEQ ID NO: 2 for a DNase I.

14. A host cell transformed with an expression vector comprising a nucleic acid encoding an amino acid sequence of SEQ ID NO: 2 for a synthetic bovine DNase I.

15. The host cell of claim 14, wherein the host cell comprises a yeast cell.

16. The host cell of claim 14, wherein the host cell comprises *Pichia pastoris*.

17. A process for making a protein with DNase activity comprising the steps of:
   transforming a host cell with an isolated nucleic acid comprising a nucleotide sequence encoding a DNase Protein with at least about an 95% identity with SEQ ID NO: 2 for a DNase; and
   culturing the host cell under conditions such that the DNase protein is produced by the host cell.

18. A synthetic bovine DNase I produced by a process comprising:
   culturing a yeast host cell transformed with an expression vector comprising a DNA sequence comprising the nucleotide sequence encoding the synthetic bovine DNase I as shown in FIG. 1 (SEQ ID NO:2),
   expressing the synthetic bovine DNase I in the cultured yeast host cell; and
   isolating the synthetic bovine DNase I.

19. A process for making a synthetic bovine DNase I comprising the steps of:
   transforming a host cell with a nucleic acid molecule that encodes the bovine DNase I comprising an amino acid sequence of SEQ ID NO: 2; and
   culturing the host cell under conditions in which the bovine DNase I is produced by the host cell.

20. The process of claim 19, wherein the host cell comprises *Pichia pastoris*.

21. The process of claim 19, wherein the host cell produces at least 1.0 mg/L bovine DNase I protein.

22. The process of claim 19, wherein the host cell produces at least 7.5 mg/L bovine DNase I protein.

23. A synthetic bovine DNase I made by the process of claim 19.

* * * * *